US008317781B2

(12) United States Patent
Owens et al.

(10) Patent No.: US 8,317,781 B2
(45) Date of Patent: Nov. 27, 2012

(54) POWER SUPPLY FOR LIGHT-BASED DERMATOLOGIC TREATMENT DEVICE

(75) Inventors: William Owens, Framingham, MA (US); Arthur Aaron, Arlington, MA (US); Douglas Ely, North Andover, MA (US); Bikram Yonjan, Somerville, MA (US); Victor Lazarev, Billerica, MA (US)

(73) Assignee: Shaser, Inc., Lexington, MA (US)

( * ) Notice: Subject to any disclaimer, the term of this patent is extended or adjusted under 35 U.S.C. 154(b) by 0 days.

(21) Appl. No.: 13/371,540

(22) Filed: Feb. 13, 2012

(65) Prior Publication Data

US 2012/0143291 A1 Jun. 7, 2012

Related U.S. Application Data

(63) Continuation of application No. 13/147,590, filed as application No. PCT/US2010/052664 on Oct. 14, 2010.

(60) Provisional application No. 61/252,369, filed on Oct. 16, 2009.

(51) Int. Cl.
*A61B 18/18* (2006.01)

(52) U.S. Cl. .................. 606/9; 606/10; 606/13; 606/17; 607/88; 607/89

(58) Field of Classification Search ................ 606/8–13, 606/16–19; 607/88–91
See application file for complete search history.

(56) References Cited

U.S. PATENT DOCUMENTS

| 4,686,986 | A | | 8/1987 | Fenyo et al. |
|---|---|---|---|---|
| 5,947,957 | A | * | 9/1999 | Morris ............................ 606/13 |
| 6,494,899 | B1 | | 12/2002 | Griffin et al. |
| 6,733,493 | B2 | * | 5/2004 | Gruzdev et al. .................... 606/9 |
| 7,935,139 | B2 | * | 5/2011 | Slatkine .......................... 607/88 |
| 2004/0054386 | A1 | | 3/2004 | Martin et al. |
| 2004/0225339 | A1 | | 11/2004 | Yaroslavsky et al. |
| 2005/0065531 | A1 | | 3/2005 | Cohen |
| 2005/0245997 | A1 | | 11/2005 | Holjo et al. |

(Continued)

FOREIGN PATENT DOCUMENTS

DE 3134953 A1 3/1983

(Continued)

OTHER PUBLICATIONS

U.S. Appl. No. 29/345,041, filed Oct. 8, 2009, entitled, "Replaceable Cartridge for Light-Based Dermatologic Treatment Devices"; 7 pages.

(Continued)

*Primary Examiner* — Ahmed Farah

(74) *Attorney, Agent, or Firm* — Guerin & Rodriguez, LLP

(57) ABSTRACT

Switching power supplies made in accordance with the disclosed technology drive flash lamps of dermatologic treatment devices to emit a sequence of relatively small light pulses that are aligned with particular locations within the waveform of the AC line source. Such power supplies not only enable sufficient light energy in aggregate to therapeutically heat target chromophores in a skin region without causing undesired damage to surrounding tissue, but also provide the added benefit that the corresponding electrical energy need not be substantially drawn from any charged capacitor. The disclosed power supply further compensates for performance degradation of the flash lamps during their usable life, by modifying its operation based on predetermined values that are indicative of flash lamp aging/efficiency characteristics. The flash lamps and their associated stored values are preferably incorporated into a replaceable cartridge that facilitates user maintenance of the dermatologic treatment device.

3 Claims, 11 Drawing Sheets

U.S. PATENT DOCUMENTS

| | | | |
|---|---|---|---|
| 2007/0198004 A1 | 8/2007 | Altshuler et al. | |
| 2008/0058783 A1 | 3/2008 | Altshuler et al. | |
| 2008/0172112 A1* | 7/2008 | Gourgouliatos et al. | 607/89 |
| 2008/0172113 A1* | 7/2008 | Gourgouliatos et al. | 607/90 |
| 2009/0146086 A1 | 6/2009 | Manstein | |
| 2009/0234342 A1 | 9/2009 | Ely et al. | |
| 2012/0010684 A1* | 1/2012 | Owens et al. | 607/88 |

FOREIGN PATENT DOCUMENTS

| | | |
|---|---|---|
| EP | 1340521 A2 | 9/2003 |
| WO | 2005030317 A2 | 4/2005 |
| WO | 2008012519 A1 | 1/2008 |
| WO | 2008057597 A2 | 5/2008 |
| WO | 2009053965 A1 | 4/2009 |
| WO | 2009109885 A2 | 9/2009 |

OTHER PUBLICATIONS

U.S. Appl. No. 12/056,612, filed Mar. 27, 2008, entitled, "Enhancing the Brightness of Optical Radiation Used in Light-Based Dermatologic Treatment Systems"; 49 pages.

Examination Report in EP counterpart Application No. EP10774051.6 dated May 3, 2012; 6 pages.

International Preliminary Report on Patentability in counterpart PCT Application No. PCT/US2010/052664 dated Apr. 26, 2012; 13 pages.

Extended Search Report in EP counterpart Divisional Application No. 12158651.5 dated Apr. 24, 2012; 9 pages.

Extended Search Report in EP counterpart Divisional Application No. 12158650.7 dated Apr. 19, 2012; 6 pages.

Extended Search Report in EP counterpart Divisional Application No. 12158652.3 dated Apr. 19, 2012; 8 pages.

Extended Search Report in EP counterpart Divisional Application No. 12158653.1 dated Apr. 19, 2012; 7 pages.

International Search Report and Written Opinion for counterpart PCT Application No. PCT/US2010/052664 dated Mar. 25, 2011; 20 pages.

Examination Report in counterpart EP Application No. 10774051.6 dated Dec. 22, 2011; 5 pages.

* cited by examiner

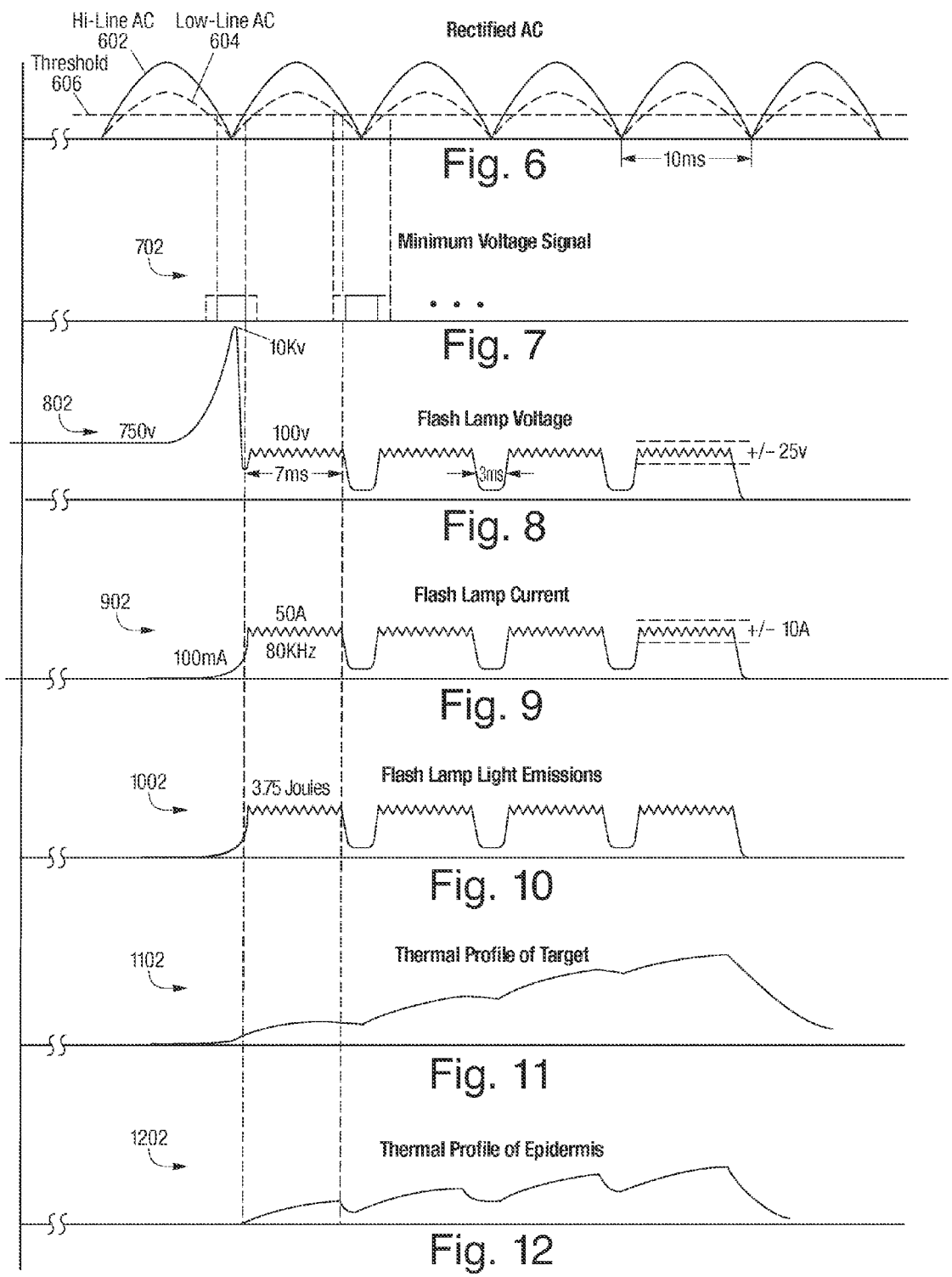

POWER SUPPLY FOR LIGHT-BASED DERMATOLOGIC TREATMENT DEVICE

RELATED APPLICATIONS

This application is a continuation of U.S. application Ser. No. 13/147,590, filed Aug. 2, 2011, which is the National Stage of International Application PCT/US 10/52664, filed Oct. 14, 2010, which claims the benefit of U.S. Provisional Application No. 61/252,369, filed on Oct. 16, 2009, the entireties of which applications are incorporated herein by reference.

TECHNICAL FIELD

The disclosed technology relates generally to power supply designs for light-based dermatologic treatment devices and more specifically to switching power supply circuits capable of repeatedly pulsing a flash lamp to emit a desired amount of therapeutic light energy in such treatment devices without any substantial electrical energy being provided by a charged capacitor.

BACKGROUND

Electromagnetic energy has been used in a wide range of medical applications for many years. In the field of dermatology, lasers, flash lamps/intense pulsed light systems (IPL), and other sources of electromagnetic radiation, particularly in the optical radiation wavebands, have been used in dermatologic treatment devices to permanently/temporarily remove hair, promote hair regrowth, treat vascular and pigmented lesions, reduce the appearance of wrinkles, treat acne, remove warts, reduce the appearance of scars, tighten skin, resurface skin, reduce cellulite, remove tattoos, and the like. Light-based dermatologic treatment devices applied to such treatments are normally designed to emit therapeutic levels of light energy in a controlled manner such that one or more light pulses applied to a skin region exhibit predetermined fluence levels, wavelength ranges, pulse durations, and inter-pulse delays to achieve a desired therapeutic result. Failure to properly control the parameters of the emitted light energy can result in poor efficacy and/or excessive damage to target/nontarget tissue.

IPL-based dermatologic treatment devices typically employ switching power supplies with pulse forming circuits (also referred to herein as pulse-drive circuits). Unfortunately the pulse forming circuitry in the prior art normally relies on one or more large capacitors that, when discharged into one or more flash lamps, provide the primary electrical energy to pulse the flash lamps to emit a therapeutically effective amount of light energy. The size, weight, and cost of these relatively large capacitors result in cumbersome and expensive treatment devices. Accordingly, continuing research and development is necessary to develop smaller, lighter, and cost-effective dermatologic treatment devices, especially in the consumer market where such concerns are particularly acute.

SUMMARY

Switching power supplies made in accordance with the disclosed technology can drive/pulse the flash lamps of IPL-based dermatologic treatment devices at sufficient levels to achieve a desired therapeutic effect without incurring the size, weight, and cost limitations of relatively large capacitive elements. By driving the flash lamps of the dermatologic treatment device to generate a sequence of relatively small light pulses ("small" with respect to fluence and/or pulse duration) aligned with particular locations within the waveform of the AC line source, the improved power supply not only enables sufficient light energy in aggregate to therapeutically heat target chromophores (e.g., melanin) in a skin region without causing undesired damage to surrounding tissue, but also provides the added benefit that the corresponding electrical energy need not be substantially drawn from any charged capacitor. Consequently, the size, weight, and cost of dermatologic treatment devices incorporating the disclosed technology can be significantly reduced.

In one illustrative embodiment, at least some aspects of the disclosed technology can be embodied within a dermatologic treatment device configured to facilitate achievement of a desired cosmetic effect in a target skin region, such as permanent/temporary hair removal, wrinkle reduction, acne reduction, wart removal, increased hair growth, reduction in pigmented or vascular lesions, reduction in appearance of scars, skin tightening, cellulite reduction, and the like. This improved device can include one or more pulse-able flash lamps capable of emitting sufficient light energy to facilitate achievement of the desired cosmetic effect. The flash lamp(s) is/are preferably pressurized with a noble gas exhibiting desired emission spectrum peaks, such as may be provided by xenon and/or krypton and can be provided at, for example, one-half atmosphere or more, one atmosphere or more, etc. In some embodiments, at least some of the light energy emitted by the flash lamp(s) can be transmitted to the skin region via an optically transparent skin contact element exhibiting a skin contact surface of 2 square centimeters or greater. The device further includes a switching power supply with at least an AC line voltage detector, a pulse-drive circuit, and a control circuit.

The AC line voltage detector is in electrical communication with an AC line source and dynamically generates a signal whose duty cycle is indicative of when the voltage of the line source meets or exceeds a minimum operating voltage threshold. This duty cycle is useful in ascertaining whether the AC line source is providing high-line or low-line AC voltage. The signal generated by the AC line voltage detector can also be indicative of the frequency of the AC line source.

The pulse-drive circuit is in electrical communication with the flash lamp(s) and the AC line source and provides sufficient electrical energy to pulse the flash lamp(s) during its/their simmer state without drawing a substantial amount of electrical energy from a charged capacitor. One or more characteristics of the electrical energy (e.g., current level, current pulse duration, and/or inter-pulse delay interval) provided by the pulse-drive circuit to the flash lamp(s) are based at least partly on the duty cycle of the signal generated by the AC line voltage detector. Consequently, the duty cycle or inverse of the duty cycle can substantially correspond to a pulse width of the emitted light energy. For example, the duty cycle of the AC line voltage exceeding the minimum operating voltage threshold can be substantially the same as or greater than a pulse width of the emitted light energy. Further, the pulse-drive circuit may include filter circuitry that mitigates the effect of electromagnetic emissions generated by the device on the AC line source, rectifier circuitry that rectifies the electrical energy provided by the AC line source, a current sensor that provides an indication of the electric current in the flash lamp(s), buck regulator circuitry that receives the rectified energy and provides corresponding regulated electric current to the flash lamp(s) under the control of the control circuit, and a switch in electrical communication with the rectifier and buck regulator that selectively enables transmission of the rectified electrical energy to the buck regulator.

The control circuit is in electrical communication with the pulse-drive circuit and AC line voltage detector and selectively enables transmission of sufficient electrical energy from the pulse-drive circuit to pulse the flash lamp(s) to emit a therapeutically-sufficient amount of light energy to facilitate achievement of the desired cosmetic effect. These selective transmissions are based at least partly on the signal generated by the voltage detector. Further, the control circuit may include a comparator in electrical communication with the switch and current sensor that generates a signal to control the switch based on a comparison between the indication from the current sensor and a reference voltage, and a microprocessor in electrical communication with the AC line voltage detector and comparator that determines the level of the reference voltage based at least partly on the duty cycle of the signal generated by the voltage detector. The microprocessor modifies the reference voltage to ensure that the flash lamp(s) emits/emit light energy within a desired fluence range. The microprocessor can further disable the pulse-drive circuit in response to a cooling system failure in the device, a high temperature condition, a user input, a failure to maintain the device in physical contact with at least one surface of the skin region, an improper configuration condition, and/or a maintenance condition.

The dermatologic treatment device may also include a simmer circuit that provides a low current density to the flash lamp(s) sufficient to enable the flash lamp(s) to maintain its/their simmer state. A diode in the pulse-drive circuit can be used to prevent any unwanted electrical energy provided during the simmer state from entering and undesirably affecting other elements of the pulse-drive circuit. The device further includes a trigger circuit that provides sufficient electrical energy to the flash lamp(s) to initiate ionization in the flash lamp(s) at the beginning of the simmer state.

The dermatologic treatment device is preferably configured such that its control circuit enables the pulse-drive circuit to pulse the flash lamp(s) in a predetermined sequence of light pulses. The sequence of light pulses can include two or more light pulses (preferably at least 3 light pulses) with individual pulse durations between about 1 microsecond and 17 milliseconds (preferably between about 4 and 6 milliseconds for systems coupled to 60 Hertz AC line sources and between about 4 and 8 milliseconds for systems coupled to 50 Hertz AC line sources) separated by, for example, an inter-pulse delay interval that is less than the thermal relaxation time of a target within the skin region, an inter-pulse delay interval that is at least as great as the thermal relaxation time of nontarget tissue (e.g., epidermis), and/or that is based at least partly on a skin type associated with the skin region. In some embodiments, the sequence of light pulses is repeated once or more times per second (preferably repeated every 0.5 to 0.75 seconds). In other embodiments, the sequence of light pulses repeats at intervals greater than one second (e.g., intervals greater than or equal to 2 seconds). In some embodiments, the sequence of light pulses is repeated at variable intervals based on, for example, one or more temperature measurements within a handheld housing that contains the flash lamp(s).

Further, the sequence of light pulses is preferably tuned for a desired cosmetic effect in a skin region. In an illustrative operation in which temporary hair removal is desired, the device can be configured such that a sequence of light pulses provides an aggregate fluence of the sequence of between about 5-10 J/cm2 (preferably between about 6-8.5 J/cm2) to a target skin region with individual pulse widths between about 3-8 ms and inter-pulse delay intervals between about 3-15 ms and including wavelengths at least in the range of about 850-1000 nm.

In another illustrative embodiment, at least some aspects of the disclosed technology can be embodied within a dermatologic treatment device that includes one or more pulse-able flash lamps, an AC line voltage detector, and a control circuit. The flash lamp(s) is selected such that it is capable of emitting sufficient light energy to facilitate achievement of a desired cosmetic effect in a skin region. The AC line voltage detector dynamically generates a signal whose duty cycle is indicative of when an AC line voltage exceeds a minimum operating voltage threshold. This minimum operating voltage threshold corresponds to an electrical energy level sufficient to pulse the flash lamp(s) (while it is in a simmer state) to emit a therapeutically effective amount of light energy to the skin region. The control circuit is in electrical communication with the AC line voltage detector and selectively enables transmission of a desired current through the flash lamp(s) based at least in part on the signal generated by the AC line voltage detector.

In yet another illustrative embodiment, at least some aspects of the disclosed technology can be embodied within a dermatologic treatment device that includes one or more pulse-able flash lamps, a memory, and a pulse-drive circuit. The flash lamp(s) is selected such that it is capable of emitting sufficient light energy to facilitate achievement of a desired cosmetic effect in a skin region. The memory stores one or more predetermined values that are indicative of one or more characteristics of the flash lamp(s). The pulse-drive circuit is in electrical communication with the flash lamp(s) and repeatedly pulses the flash lamp(s) (while it is in a simmer state) to emit a therapeutically effective amount of light energy to the skin region. The electrical energy provided by the pulse-drive circuit to the flash lamp(s) does not include any substantial electrical energy from a charged capacitor and is based at least partly on the predetermined value(s) stored in the memory.

In yet another illustrative embodiment, at least some aspects of the disclosed technology can be embodied within a dermatologic treatment device that includes one or more flash lamps, a memory, and a switching power supply. The memory stores one or more predetermined values that are indicative of one or more characteristics of the flash lamp(s). The switching power supply is capable of repeatedly pulsing the flash lamp(s), unrestricted by any capacitor recharge duration and without relying on any substantial energy from a charged capacitor, with sufficient electrical energy to drive the flash lamp(s) to emit a sequence of light pulses sufficient to facilitate achievement of a desired cosmetic effect in a skin region. Further, the amount of electrical energy provided by the switching power supply is based at least partly on the predetermined value(s) stored in the memory.

In yet another illustrative embodiment, at least some aspects of the disclosed technology can be embodied within a dermatologic treatment device that includes one or more pulse-able flash lamps, an AC line voltage detector, and a pulse-drive circuit. The AC line voltage detector is in electrical communication with an AC line source and dynamically generates an indication of when the AC line voltage meets, exceeds or is below a minimum operating voltage threshold. The pulse-drive circuit provides pulsed electrical energy to the flash lamp, which drives the lamp to emit sufficient pulsed light energy to facilitate achievement of a desired cosmetic effect in a skin region. The pulse width of the pulsed light energy can be made variable based on the indication generated by the AC line voltage detector.

In yet another illustrative embodiment, at least some aspects of the disclosed technology can be embodied within a dermatologic treatment device that includes a source of optical radiation (e.g., one or more lasers, light emitting diodes, flash lamps and/or other types of lamps or light emitting elements), a handheld housing containing the optical radiation source, a temperature sensor that senses one or more temperatures within the housing (where such temperatures are substantially affected by operation of the optical radiation source), a power supply circuit that drives the optical radiation source, and a control circuit that controls the power supply based, at least partly, on the sensed temperature. More particularly, the power supply circuit is capable of repeatedly pulsing the optical radiation source such that the optical radiation source emits a first sequence of light pulses that are sufficient to facilitate achievement of a desired cosmetic effect in a skin region. Further, the control circuit can selectively enable the power supply circuit to pulse the optical radiation source to emit a second sequence of light pulses, where the time interval between the first and second sequences of light pulses is variable based on one or more temperatures sensed within the handheld housing by the temperature sensor.

In yet another illustrative embodiment, at least some aspects of the disclosed technology can be embodied within a dermatologic treatment device that includes one or more flash lamps, a memory (e.g., EEPROM) storing one or more predetermined values indicative of one or more characteristics of the flash lamp(s), a replaceable cartridge that contains the flash lamp(s) and memory and facilitates periodic replacement of the flash lamp(s), a power supply capable of energizing the flash lamp to emit optical radiation sufficient to facilitate achievement of a desired cosmetic effect in a skin region, and a control circuit in communication with the power supply and memory that periodically causes the power supply to increase the electric current provided to the flash lamp(s) based at least partly on the predetermined value stored in the memory. One or more predetermined values stored in the memory can be indicative of an aging characteristic (e.g., gradual reduction in light output) of the flash lamp(s) and/or of an efficiency of the flash lamp(s).

In yet another illustrative embodiment, at least some aspects of the disclosed technology can be embodied within a replaceable cartridge for a light-based dermatologic treatment device, where such replaceable cartridge includes one or more flash lamps and a memory mechanically coupled to the flash lamp(s) (mechanical coupling can be achieved, for example, using a housing of the cartridge that maintains a relative position between the flash lamp(s) and memory). The memory stores one or more predetermined and/or dynamically-generated values that are indicative of one or more characteristics of the flash lamp(s), such as an aging characteristic, an efficiency, a range of filtered wavelengths emitted by the flash lamp(s) (in which case it is preferable that the replaceable cartridge is designed for a particular range of skin colors or skin types), a maximum flash count of the flash lamp(s), and/or an initial amount of electric current necessary to drive the flash lamp(s) to emit optical radiation sufficient to facilitate achievement of a desired cosmetic effect in a skin region. A predetermined value stored in memory can also be indicative that the flash lamp(s) contained in the replaceable cartridge is/are authorized for use in such replaceable cartridge. The housing of the replaceable cartridge contains the flash lamp and memory and further includes a vent portion exhibiting a louvered or herringbone cross section, which facilitates cooling of the flash lamp while concurrently blocking at least some light emissions leaking out of the electrode ends of the flash lamp.

In yet another illustrative embodiment, at least some aspects of the disclosed technology can be embodied within a dermatologic treatment device that includes one or more pulse-able flash lamps that are capable of emitting sufficient light energy to facilitate achievement of a desired cosmetic effect in a skin region, along with a window adapted to insulate a skin surface in the skin region from at least some of the unwanted heat generated during operation of the device. The window preferably includes a first pane and a second pane of optically transparent material with a sealed space defined therebetween. The second pane may include reflective coatings that reflect at least some of the light emissions with wavelengths less than about 600 nanometers back to the flash lamp and is preferably comprised of an optically transparent material that absorbs at least some of the flash lamp's infrared emissions (e.g. above about 2000 nanometers). The first pane is preferably comprised of optically transparent material with a hydroxyl component of less than or equal to about 5 parts per million and is adapted for placement against a skin surface in the skin region to be treated by the device. The sealed space between the two panes can enclose a vacuum or a quantity of air or other gas.

In yet another illustrative embodiment, at least some aspects of the disclosed technology can be embodied within a dermatologic treatment device that includes one or more pulse-able flash lamps that are capable of emitting sufficient light energy during a pulse state to facilitate achievement of a desired cosmetic effect in a skin region, along with a reflector, optical waveguide, and optically transparent window. The reflector is optically coupled to the flash lamp(s) and is adapted to reflect at least some of the light energy emitted by the flash lamp(s). The optical waveguide is optically coupled to the reflector and is adapted to convey at least some of the light energy reflected by the reflector. The optically transparent window is optically coupled to the optical waveguide and is adapted to receive at least some of the light energy conveyed by the waveguide. The optical waveguide is normally spaced apart from the reflector and/or window by a predetermined distance when the flash lamp is not in its pulse state, but that distance is substantially reduced, and in some embodiments substantially eliminated, when the flash lamp is in its pulse state (e.g., when emitting one or more sequences of intense pulsed light). Maintaining the distance at a predetermined value when the flash lamp(s) is not emitting a light pulse sequence facilitates cooling of the device, whereas a substantial reduction in the distance during emission of the light pulse sequence improves optical efficiency of the device at the expense of temporarily decreasing cooling of at least part of the device.

BRIEF DESCRIPTION OF THE DRAWINGS

The foregoing discussion will be understood more readily from the following detailed description of the disclosed technology, when taken in conjunction with the accompanying drawings, the same or related reference numerals being used for like elements in the various drawings, in which:

1, where FIGS. 2A and 2B depict the front of the cartridge, FIGS. 2C-2E depict the back of the cartridge along with illustrative pin out configurations, and FIGS. 2F-2G depict cross sectional views of the cartridge with illustrative louvered or herringbone-shaped vent schemes;

FIG. 6 is a signal diagram illustrating high-line and low-line AC voltage conditions that may appear on a rectified AC line source relative to a minimum operating voltage threshold sufficient to operate the dermatologic treatment device of FIG. 4;

FIG. 7 is a signal diagram of an illustrative signal generated by an AC line voltage detector, which is indicative of the frequency and high/low-line AC voltage conditions of the rectified AC line source shown in FIG. 6;

FIG. 8 is a signal diagram representing an illustrative voltage waveform applied across one or more flash lamps in a light-based dermatologic treatment device in response to operating the simmer, trigger, and pulse-drive circuits of FIGS. 13-15 under the control of the control circuit of FIG. 16 and pursuant to the methodology depicted in FIG. 5;

FIG. 9 is a signal diagram representing an illustrative current waveform passing through one or more flash lamps and corresponding to the voltage waveform shown in FIG. 8;

FIG. 10 is a signal diagram representing the light emitted by one or more flash lamps when such flash lamps are subjected to the voltage and current waveforms of FIGS. 8 and 9;

FIG. 11 provides an illustrative thermal profile of target tissue located in a skin region below the epidermis when subjected to the light emissions depicted in FIG. 10;

FIG. 12 provides an illustrative thermal profile of non-target, epidermal tissue when subjected to the light emissions depicted in FIG. 10;

DETAILED DESCRIPTION

Figure 1:
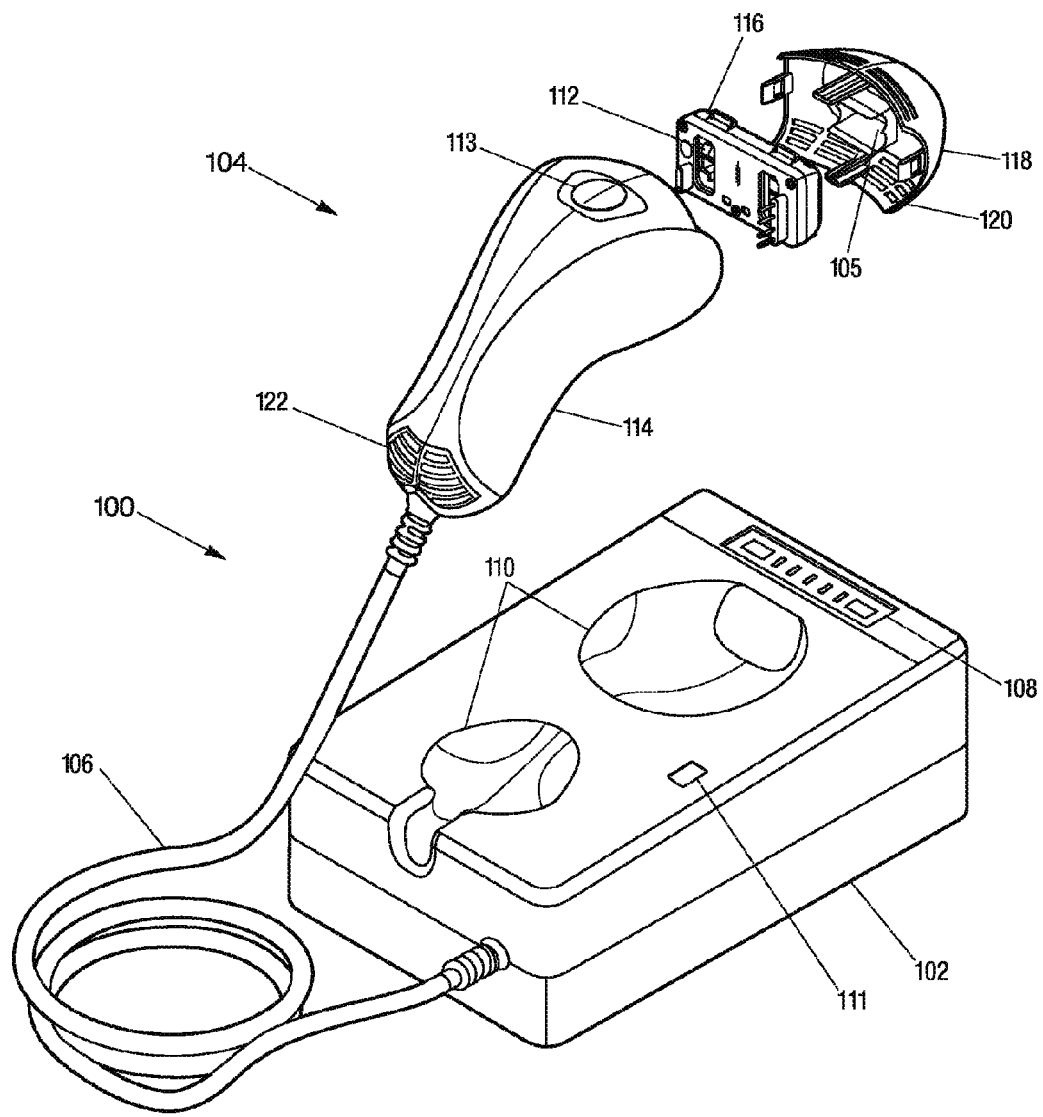
FIG. 1 provides a three dimensional perspective of an illustrative dermatologic treatment device made and operated in accordance with at least some aspects of the disclosed technology.

Unless otherwise specified, the illustrated embodiments can be understood as providing exemplary features of varying detail of certain embodiments, and therefore, unless otherwise specified, features, components, modules, elements, circuits, and/or aspects of the illustrations can be otherwise combined, interconnected, sequenced, separated, interchanged, positioned, and/or rearranged without materially departing from the disclosed systems or methods. Additionally, elements illustrated in the drawings are provided primarily to facilitate understanding of the disclosed technology and are not necessarily drawn to scale.

For the purposes of this disclosure, the term "circuit" refers to an interconnection of electrical (analog or digital), electronic, optical, acoustic, mechanical, magnetic, electromechanical, electro-optical, optoelectronic, photonic, electromagnetic, and/or electro-acoustic elements or the like arranged in substantially any suitable manner or combination to perform one or more desired functions. Those skilled in the art will recognize that the functionality described for a particular circuit can be incorporated into one or more other circuits, that particular elements in a circuit can be shared with different circuits, and/or that the circuits themselves can be otherwise combined, interconnected, separated, and/or organized without adversely affecting the operation of the disclosed technology and thus are intended merely for illustrative purposes.

Except as explicitly stated to the contrary, the term, "substantially" can be broadly construed to indicate a precise relationship, condition, arrangement, orientation, and/or other characteristic, as well as, deviations thereof as understood by one of ordinary skill in the art, to the extent that such deviations do not materially affect the disclosed methods and systems.

Further, the terms "light" and "optical radiation" are used interchangeably and references to "wavelengths" pertain to optical radiation exhibiting wavelengths of the type described in that context. The terms "device" and "system" are also used interchangeably, as are the terms "circuit" and "supply."

Light-based dermatologic treatment devices typically rely on the spectral emissions of one or more lasers, flash lamps, and/or LEDs to provide sufficient optical radiation to thermally treat a desired epidermal or dermal condition. Flash lamps, in particular, provide a flexible and cost effective means for generating intense pulsed light exhibiting a range of desired wavelengths that can be tuned (by filtration and/or wavelength conversion) to facilitate a desired cosmetic or non-cosmetic effect in a target skin region.

Flash lamps are gas discharge devices having an optically transparent envelope (made of, for example, fused quartz/silica, borosilicate, or the like) that is sealed on each end to an electrode assembly and filled with a noble gas (e.g., xenon, krypton, etc.) to a desired pressure (e.g., one-half atmosphere, one atmosphere, etc). Prior to emitting optical radiation, the impedance of the flash lamp is initially relatively high due to the resistivity of the unionized noble gas between the cathode and anode. In order to emit optical radiation, the gas in the flash lamp must be ionized, which will also result in a drastically reduced impedance.

Such ionization can be instantiated by applying a high voltage trigger pulse (e.g., 6-10 kilovolts for 200 nanoseconds to 1 millisecond) to the electrode assembly of the flash lamp using an external, series injection, or pseudo-series injection triggering scheme, as is known to those skilled in the art. Once the gas is ionized, it emits optical radiation across a broad spectrum of wavelengths. The amount of optical radiation emitted is dependent, at least in part, on the degree of ionization of the gas, which is affected by the electrical current density supplied between the electrodes following the trigger pulse. Higher current densities result in intense light emissions (referred to herein as the "pulse state" of the flash lamp), while lower current densities cause the ionized gas to appear as a thin streamer of light between the electrodes of the flash lamp (referred to herein as the "simmer state" of the flash lamp). The lifetime of the flash lamp decreases as the duration and peak of electrical energy provided during the pulse state increases, with the flash lamp eventually failing via a catastrophic explosion, fracturing of its optically transparent envelope, or by a gradual reduction in emitted light. When a sequence of intense light pulses is desired, the flash lamp is preferably operated in a simmer state, or at a relatively low-intensity level in a pulse state, during the inter-pulse period so as to reduce the thermal and mechanical shock to the flash lamp, thereby extending its usable life.

Designers of flash lamp based dermatologic treatment devices expend significant effort in developing power supplies capable of driving flash lamps to emit optical radiation exhibiting a desired pulse profile while concurrently maintaining reliable power supply performance, commercially-reasonable life expectancy of the flash lamps, and a low device/power supply cost. These competing interests are difficult to reconcile and have driven prior art device manufacturers to use expensive, capacitor-based power supplies that store large amounts of electrical energy that drive the flash lamps under microprocessor control—thereby heavily favoring generation of a desired light pulse profile over device/power supply cost. It is important to note that prior art devices have traditionally been operated in a clinical setting, where cost is an important, but secondary, factor. In contrast, the commercial success of devices targeted at the consumer market is dependent upon achieving adequate treatment efficacy at a much lower cost.

The inventors recognize that there are several light pulse sequences available for any particular dermatologic treatment and that judicious selection amongst these sequences (and careful timing when instantiating such light pulse sequences relative to the input AC waveform) can be made, such that the electrical energy provided by a power supply to drive the flash lamp(s) during its pulse state can be drawn substantially directly from the AC line and without any substantial electrical energy being provided from charged capacitors (e.g., less than about 10% of the required electrical energy being provided by capacitors with the remainder being drawn from the AC line), thereby resulting in a low cost and effective dermatologic treatment device that is commercially viable for the consumer market. For example, the disclosed technology can be incorporated within an illustrative light-based, dermatologic treatment device targeted at temporary hair removal where the AC line source provides 120 volts at 60 Hz (each half cycle being 8.3 milliseconds in duration) in which case the device can be configured to emit a light pulse sequence having a plurality of pulses (e.g., 4 pulses) providing an aggregate fluence on a skin treatment surface of between about 6-8.5 Joules per square centimeter with each pulse exhibiting a pulse width of up to about 5.8 milliseconds (corresponding to that portion of the 8.3 millisecond AC half cycle above an illustrative minimum operating voltage threshold) and inter-pulse delay of about 2.5 milliseconds (corresponding to that portion of the AC half cycle dropping below the minimum operating voltage threshold after the peak of the cycle together with the portion of the next AC half cycle that rises up to the minimum operating voltage threshold). The selection of this illustrative light pulse sequence enables the bulk of the electrical energy supplied to the flash lamp during its pulse state to be drawn substantially directly from a full wave, rectified AC line source during a period in which the voltage of the AC line is greater than or equal to about 107 volts (corresponding to an illustrative minimum operating voltage threshold). Similarly, an illustrative light pulse sequence (comprising, for example, 3 pulses) in which each pulse has a duration of up to about 7 milliseconds with an inter-pulse delay of about 3 milliseconds is suitable in situations where the AC line source provides 240 volts at 50 Hz (each half cycle being 10 milliseconds in duration).

Further, the disclosed technology can be configured to provide a fixed pulse width for each of the individual pulses in the light pulse sequence and/or a fixed aggregate pulse width for the light pulse sequence itself to ensure repeatability of tightly-controlled treatment energy parameters during the same or different treatment sessions. For example, in a scenario where fixed pulse widths are desired, the disclosed technology initially determines whether that portion of the AC half cycle above a minimum operating voltage is of sufficient duration to support the pulse width of the electrical energy used to pulse one or more flash lamps in the dermatologic treatment device. If sufficient duration is found in the AC half cycle, the disclosed technology operates the dermatologic treatment device such that it drives the flash lamp to emit therapeutic levels of optical radiation during the period of time in which the AC half cycle is at or above the minimum operating voltage. If the duration of the AC half cycle is insufficient to drive the flash lamps as desired, an error condition is identified and reported to a user of the dermatologic treatment device.

Similarly, it may be advantageous to have some variability in the pulse widths of individual pulses so long as the aggregate pulse width of the light pulse sequence remains fixed. For example, the pulse width of the first pulse in the light pulse sequence may be somewhat shorter than those of the other pulses in that the first pulse is instantiated near the peak of an AC half cycle (substantially above the minimum operating voltage threshold) to facilitate triggering of the flash lamps without sacrificing the aggregate amount of therapeutic optical radiation applied to a target skin treatment region by the light pulse sequence.

Alternatively, the disclosed technology can be configured in a more flexible arrangement to provide variable pulse widths for individual pulses and/or for the light pulse sequence itself to dynamically account for sagging or "low line" conditions that may occur on the AC line source, flash lamp degradation, varying skin types between skin treatment regions, or in other situations where operating or treatment conditions are likely to vary. For example, and in order to operate properly under the different high or low line conditions that may be encountered on an AC line source, the disclosed technology can include an AC line voltage detector that dynamically identifies that portion of the AC half cycle that exceeds a minimum operating voltage threshold regardless of the specific condition of the electrical energy received via an AC line source and then uses a processor to determine (via computation, table lookup, or otherwise) suitable pulse widths, inter-pulse delays, and/or pulse sequences that are capable of driving one or more flash lamps to emit a therapeutically effective amount of light energy to a skin region of interest.

Further, the disclosed technology can modify a minimum operating voltage threshold in response to flash lamp degradation/aging characteristics such that the threshold is periodically increased to more readily provide greater electrical current thereby driving the flash lamps harder to provide a relatively consistent light output as the flash lamps age/degrade. This functionality can be facilitated by providing a memory that stores indicia pertaining to flash lamp aging/degradation characteristics along with other useful information (e.g., flash lamp efficiency, maximum flash count, current flash count, initial amount of electrical current desired to drive the flash lamp to emit therapeutic levels of optical radiation, a range of filtered wavelengths emitted by the flash lamp, manufacturing batch information, indicia pertaining to other portions of an optical subsystem, and/or the like). In embodiments incorporating such memory, it is desirable to include the flash lamp(s) and memory within a replaceable cartridge that can be readily inserted into or removed from the dermatologic treatment device.

The disclosed technology can also vary the aggregate duration of the light pulse sequence itself (e.g., by inserting greater inter-pulse delays between individual pulses that are somewhat larger than multiples of the duration of the applicable AC half cycle, or inserting more individual pulses) to accommodate different thermal relaxation times of target and nontarget tissue (e.g., lengthen the duration of inter-pulse delays for darker skin types) and/or different dermatologic treatments. In some embodiments, a single light pulse sequence is applied to a skin treatment region during a treatment session, whereas in other embodiments more than one light pulse sequence may be applied to part of or all of the same skin treatment region during the treatment session.

The rate at which light pulse sequences are repeated during operation of an illustrative dermatologic treatment device can be based at least partly on a momentary press of a button that results in the emission of a single light pulse sequence (particularly useful when relatively small/limited regions of skin, e.g., between about 1-6 square centimeters, are to be spot treated) or on a momentary/sustained button press when safety interlock components remain engaged for an extended period of time resulting in the emission of repeating light pulse sequences (particularly useful when treating larger skin areas, e.g., greater than about 6 square centimeters). The repeating light pulse sequences can, in some illustrative embodiments, occur at intervals greater than or equal to about 2.25 seconds, but preferably occur at shorter intervals such as between about 0.4-1 second and most preferably between about 0.5-0.75 second so that the therapeutic light energy can be applied to adjacent skin treatment regions in a gliding fashion.

In brief overview, and with reference now to FIG. 1, at least some aspects of the disclosed technology can be embodied within an illustrative dermatologic treatment device 100 having a base 102 and a hand piece 104 interconnected by a flexible cable 106 preferably of about 5 feet or more in length. The device 100 also includes a power cable (not shown) interconnecting the base 102 with an AC line source (not shown). The device 100 is preferably sized to facilitate easy storage and transport in an end user environment (e.g., within a user's home, a hotel room, or the like) and in one illustrative embodiment exhibits dimensions of less than about 9.5 inches in length, less than about 6.5 inches in width, and less than about 3.5 inches in height (or less than about 6 inches in aggregate height when the hand piece 104 is inserted into its cradle 110 on the base 102).

The housing of the base 102 is preferably made of a plastic material and encloses a switching power supply (discussed more fully below) suitable for driving one or more flash lamps 112 in the hand piece 104 to emit a desired therapeutic light profile, as well as a user interface 108 providing a user with status information (e.g., normal/error operating conditions, indicia of remaining flashes, operating modes, indicia pertaining to the suitability of the device 100 for a user's skin type, or the like), as well as control features that enable or facilitate control and operation of the device 100 (e.g., power level settings, operating mode selector, skin type detector 111, or the like).

The housing of the hand piece 104 is also preferably made of a plastic material and encloses a cooling system (e.g., a variable-speed fan), temperature measurement components, user interface components (e.g., flash initiation button 113), safety interlock components (e.g., capacitive or mechanical skin contacting elements), an optical system (including, for example, one or more flash lamps 112, a curved, angular, or flat specular/diffusive reflector, an optical waveguide 105, and/or an optically transparent window), and/or the like. Although the hand piece 104 can be configured such that it is not serviceable by an end user, it is preferable to configure the hand piece 104 such that its handle 114, replaceable light cartridge 116, and/or nose cap 118 can be separated to facilitate periodic maintenance and repair. The handle 114 preferably includes the cooling system, temperature measurement components, and user interface components. The replaceable light cartridge 116 preferably includes one or more flash lamps 112 (which may contain particular reflective coatings thereon to filter out undesired wavelengths), a reflector, and a memory (not shown) storing one more characteristics of the flash lamps 112. The nose cap 118 preferably includes the optical waveguide 105 (e.g., a substantially rectangular, hollow and specular light pipe preferably having a silver coating and a length of at least about 15 millimeters), optically transparent window (which may contain reflective coatings thereon), and safety interlock components. In some embodiments, the components within the replaceable light cartridge 116 can be incorporated into and be an integral part of the nose cap 118, such that the integrated nose cap serves as a single user replaceable component, rather than having separately-replaceable light cartridges and nose caps.

During a dermatologic treatment session, the portion of the front, exterior housing of the nose cap 118 through which optical radiation is passed is positioned substantially against the skin such that the skin contact elements detect the proximity of the housing to the skin treatment region of interest and safely enable operation of the device 100. The light emitted by the flash lamp(s) 112 is filtered (passing wavelengths, for example, greater than about 600 nanometers, and preferably greater than 650 nanometers) and conveyed through the optically transparent window of the nose cap 118 so that it impinges on the skin treatment region. Operation of the flash lamp(s) 112 in a pulse state generates a significant amount of heat that needs to be dissipated by the cooling system. Unfortunately, cost-effective, air-cooled devices 100 suitable for the consumer market are not very efficient at removing this heat and thus it is possible that the window in the nose cap may reach a temperature that exceeds a threshold suitable for placement against a skin surface. Accordingly, air-cooled, dermatologic treatment devices 100 directed at the consumer market should either be operated in a manner that prevents overheating if the window is placed in contact with the skin (e.g., reduce the flash rate of the flash lamps 112 by increasing the time period between successive light pulse sequences so that the cooling system has sufficient time to cool the window), recess the window within the housing of the nose cap 118 (by at least, for example, 4 millimeters, for a window of about 2 square centimeters) so that the window does not come into contact with the skin during a treatment session, or provide a configuration that insulates the window contacting the skin from heat sources (e.g., the flash lamp 112 and/or metallic light pipe 105).

In this last scenario, the window can be configured as a double pane window with a sealed space between the two panes. This sealed space can enclose a partial vacuum, a gas such as xenon, or just air. The inner pane closest to the flash lamp(s) 112 preferably includes reflective coatings to filter out at least some undesirable wavelengths (e.g., wavelengths below about 600 nanometers and/or above 1200 nanometers, for a hair removal/reduction dermatologic treatment) and is made of borosilicate with a substantial hydroxyl component (e.g., greater than about 100 parts per million), whereas the outer pane designed for placement substantially against the skin is preferably made of a specialized composition of fused quartz/silica exhibiting a relatively low hydroxyl component (e.g., less than about 50 parts per million and preferably less than or equal to about 5 parts per million). In this manner the relatively high hydroxyl composition of the inner pane itself supplements the filtration capabilities of the reflective coatings thereon by absorbing some of the undesirable infrared emissions above 2000 nanometers, while enabling any remaining low-level infrared emissions (between about 2000-4000 nanometers or higher) to pass through the outer pane substantially unimpeded and without unduly raising the temperature of the outer pane. The remaining undesirable infrared emissions that pass through the outer pane and onto the skin are at a significantly reduced fluence and are not harmful to the skin and do not otherwise adversely impact the efficacy of the dermatologic treatment. Those skilled in the art will recognize that the number of panes in the window can be more than two and/or that the space between panes can be open (i.e., not sealed on at least 2 sides) to provide for a flow of cooling air, gas, or liquid to pass therebetween.

In addition to preventing overheating of the skin, air cooled dermatologic treatment devices 100 must further maintain the temperature of its components within a safe operating range without allowing excessive light leakage (e.g., more than about 3 joules) that may detract from a user's experience when operating the device 100. One or more temperature sensors within the hand piece 104 and/or base 102 can generate signals indicative of excessive or near-excessive temperatures which can be mitigated by, for example, entering a cool-down mode in which the device 100 is prevented from driving its flash lamp(s) 112 into a pulse state until a predetermined safety temperature is achieved, increasing the speed of the fan in the hand piece 104 and/or base 102, and/or reducing the rate at which light pulse sequences are repeated.

Judicious selection in the amount, orientation, location, and configuration of air inlet/outlet vents 120/122 in the hand piece 104 can be made to ensure a desired airflow while concurrently preventing excessive light leakage. For example, air inlet vents 120 can be positioned on the nosecap 118 of the hand piece 104 with air outlet vents 122 positioned substantially about the cable end of the hand piece 104, thereby venting relatively hot exhaust air in a direction away from the skin treatment region. At least some of the vents that are more likely to be subjected to light energy that has undesirably leaked out of the electrode ends of the flash lamp(s) 112 and/or out of the gap between the flash lamp 112 and waveguide 105 during operation of the device 100 are preferably configured to enable the passage of cooling air while concurrently reducing or substantially eliminating the transmission of this leaked light energy outside of the hand piece 104 using, for example, louvered or herringbone shaped vents. The vents can be made of a reflective material (e.g., white teflon, aluminum, etc.) to reflect at least some of the leaked light back into the interior of the hand piece 104 or can be made of an absorptive material (e.g., pigmented plastic) such that at least a substantial amount of the leaked light impinging on the vent is absorbed. Alternatively or in combination, vents exhibiting such louvered, herringboned, or other suitably shaped configuration can form part of the replaceable cartridge 116 so as to substantially trap the leaked light before it exits the cartridge. The benefits of incorporating such vents into the replaceable cartridge 116 include reducing the amount of heat transmitted to other hand piece elements due to their absorption of the leaked light and, in the case where the vent is made of a reflective material, redirect at least some of the leaked light back into the desired optical path such that the overall fluence on the skin treatment region is increased.

FIGS. 2A-2G provide various perspective views of an illustrative replaceable light cartridge 116 with dual flash lamps 112 that can be used in the dermatologic treatment device 100, while FIGS. 3A-3E provide analogous views of an illustrative replaceable light cartridge 116 with a single flash lamp 112. More particularly, FIGS. 2A-2B and 3A-3B depict the front (i.e., light emitting side) housing of the cartridge 116 in which a substantially open area 202 is defined, corresponding to the location of the arc of the flash lamp(s), which enables transmission of light energy substantially unimpeded into the adjacent optical waveguide 105 (FIG. 1). The vent configuration of this illustrative embodiment enhances the structural support of the cartridge 116 and enables a desired air flow to pass therethrough, while concurrently preventing a user from touching potentially hot flash lamp(s) 112 in the vicinity of their electrodes.

Figure 2A:
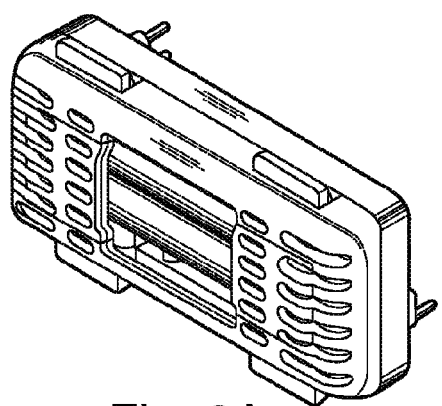
FIGS. 2A-2G provide various perspective views of an illustrative replaceable light cartridge with dual flash lamps that can be used in the dermatologic treatment device of FIG.
Figure 2B:
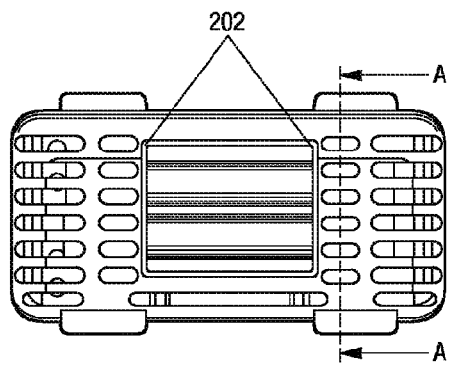
Figure 2C:
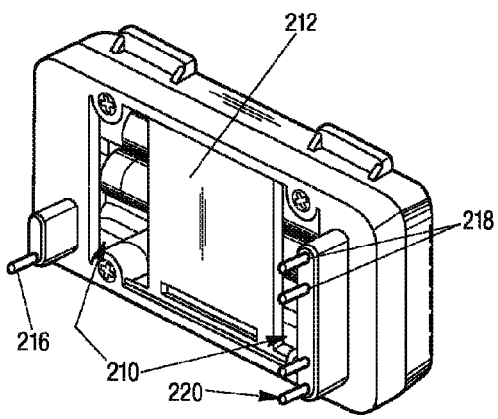
Figure 2D:
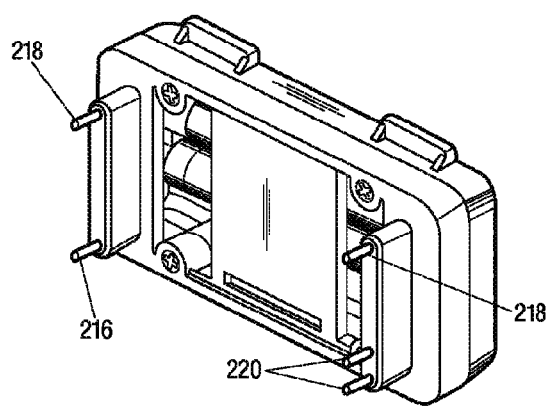
Figure 2E:
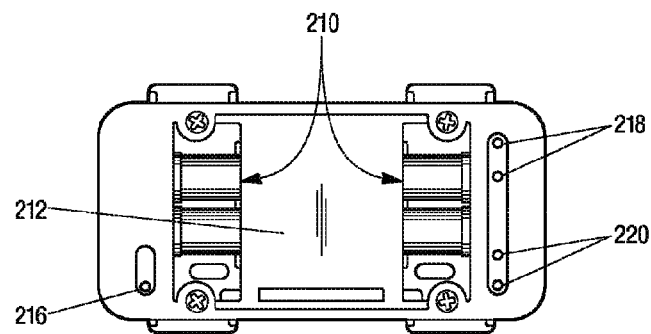
Figure 2F:
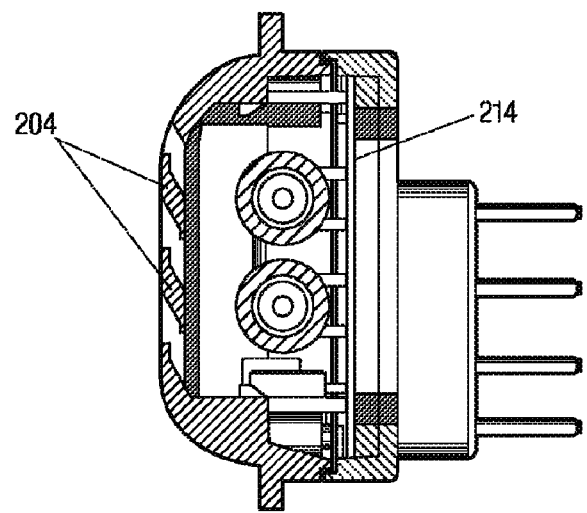
Figure 2G:
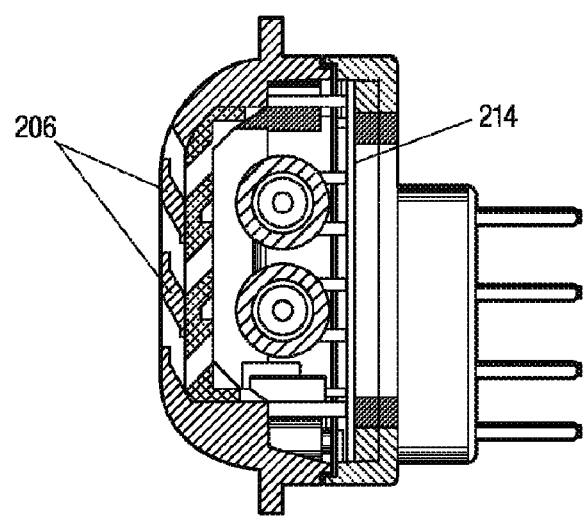

The louvered vents 204 of FIG. 2F are further tailored to block (i.e., reflect back and/or absorb) more of the light energy that undesirably leaks out of the electrode ends of the flash lamp(s) 112 without significantly restricting the air flow passed over such flash lamp(s) 112. Similarly, the herringbone shaped vents 206 of FIG. 2G are adapted to block even more leaked light than the louvered vents of FIG. 2F, albeit by sacrificing some air flow. The louvered and herringbone vents 204, 206 depicted in FIGS. 2F and 2G are shown in connection with a dual flash lamp configuration, but they can also be incorporated into the front housings of replaceable light cartridges 116 having a single flash lamp 112 or more than two flash lamps 112. Although the louvered vents 204 and herringbone vents 206 are depicted as running horizontally along the front housing of the replaceable light cartridge 116, they can be oriented vertically or at substantially any angle in the front housing without adversely affecting operation of the device 100. Further, the louvered and herringbone vents 204, 206 can include more such vents stacked one in front of the other in the same or different alignment/configuration to thereby create a labyrinth that substantially impedes the passage of leaked light without unduly sacrificing air flow necessary to cool the flash lamp(s) 112 and other elements of the replaceable cartridge 116. Light blocking vents that permit passage of a desired air flow can also be configured in a variety of other shapes and configurations, such as undulating, mesh, hexagonal, or honeycombed configurations or the like.

Figure 3A:
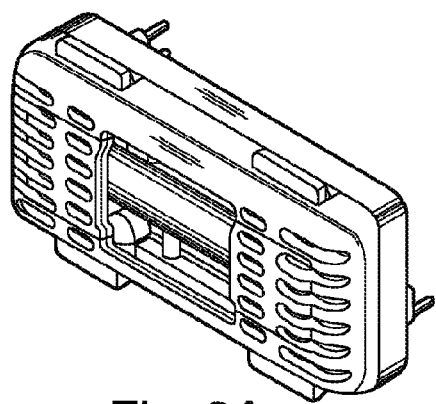
FIGS. 3A-3E are substantially identical to FIGS. 2A-2E except that they illustrate an exemplary embodiment in which the replaceable light cartridge contains a single flash lamp.
Figure 3B:
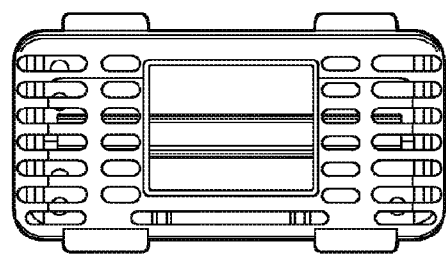
Figure 3C:
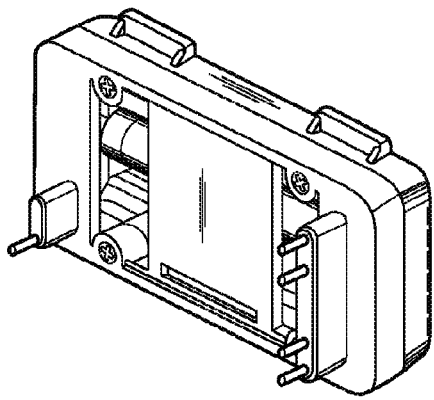
Figure 3D:
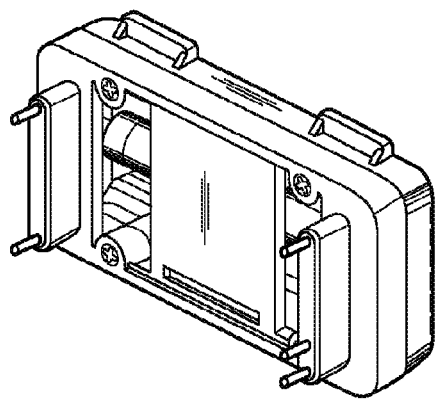
Figure 3E:
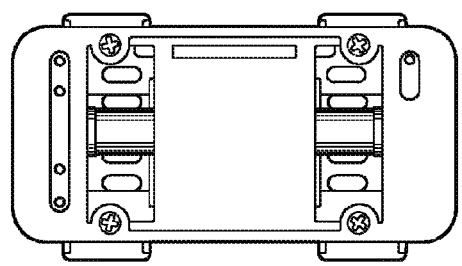

FIGS. 2C-2E and 3C-3E illustrate an exemplary housing in the rear side of the replaceable cartridge 116 shown in FIGS. 2A-2B and 3A-3B. This portion of the housing defines two substantially open regions 210 that facilitate passage of cooling air over the flash lamp(s) and other parts of the cartridge 116. The substantially centered region 212 of the rear housing, between the open regions 210, positions a reflector 214 (FIG. 2G) in fixed proximity to the flash lamp(s). Although this reflector 214 is depicted as flat, it can assume a variety of curved, angular, dimpled, or other shapes/configurations and can be made of a diffusive or specular material. The rear housing also includes a trigger pin 216 that is used to convey an electrical trigger pulse sufficient to ionize the gas in the flash lamp(s) 112, anode and cathode pins 218 that convey an electric current sufficient to maintain a simmer state and pulse state in the flash lamp(s) 112, and input-output pins 220 of a memory (not shown) that stores flash lamp characterization data useful in operating the flash lamp(s) 112 and device 100 (particularly as the light output of the flash lamp(s) 112 degrades over time). Those skilled in the art will recognize that the particular placement of these pins 216-220 are merely illustrative and that a variety of pin placements are possible; for example, the anode and cathode pins 218 can be located in proximity to each other as shown in FIGS. 2C, 2E, 3C, and 3E or can be located on opposite sides of the rear housing as shown in FIGS. 2D and 3D.

Figure 4:
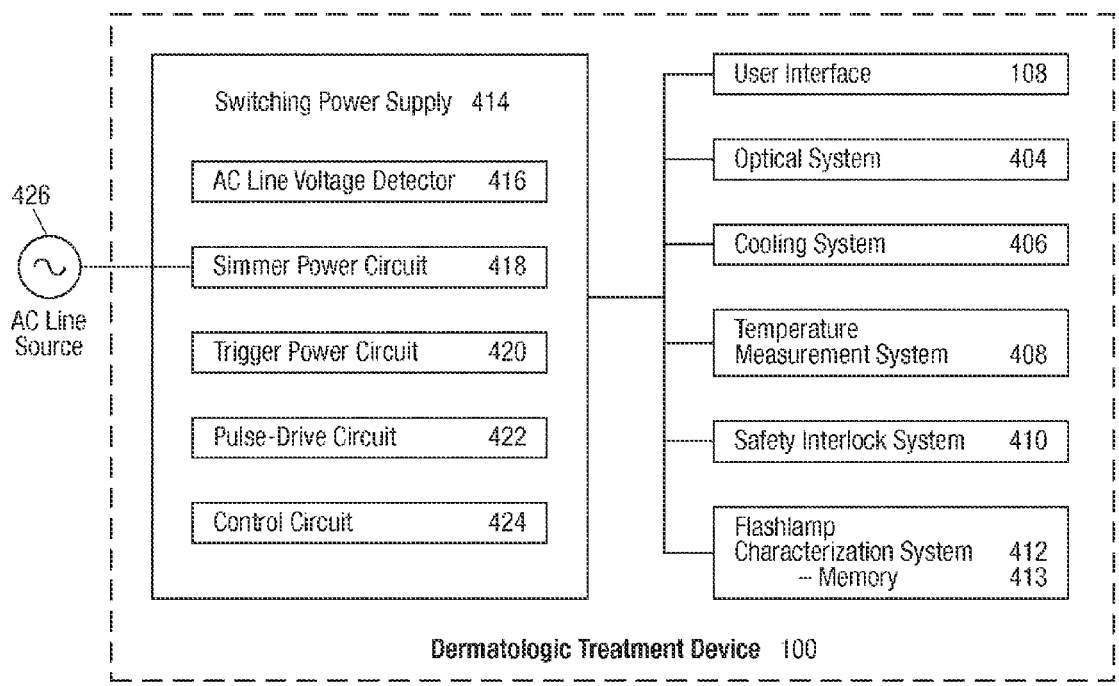
FIG. 4 provides a high level system diagram of a dermatologic treatment device incorporating an illustrative switching power supply operating in accordance with an embodiment of the disclosed technology.

In more detail, and with reference now to FIGS. 1 and 4, an illustrative, flash lamp-based dermatologic treatment device 100 made in accordance with the disclosed technology includes a user interface 108 that enables a user to interact with the device 100, an optical system 404 that generates and conveys a therapeutic amount of optical radiation to a skin treatment region, a cooling system 406 that maintains operation of the device 100 within desired operating temperatures, a temperature measurement system 408 that detects over-temperature conditions, a safety interlock system 410 that prevents inadvertent emissions of optical radiation and other hazardous occurrences, a flash lamp characterization system 412 that serves as a basis for dynamically adjusting electrical operating parameters during operation of the device 100 in response to flash lamp or other optical system 406 properties, and a switching power supply 414 that draws electrical energy from an AC line source 426 and conditions such energy to drive the optical system 404 in a desired manner.

The user interface 108 presents a user of the device 100 with selections concerning the desired operation of the device 100 (e.g., one or more power level settings that concurrently affect both the efficacy of the dermatologic treatment and the user's sensation experienced during the performance of such treatment; settings that operate the device 100 in a pulse mode where a single light pulse sequence is emitted or in strobe mode where a plurality of light pulse sequences are emitted in a predetermined sequential manner; and/or the like), as well as with the ability to initiate a dermatologic treatment (e.g., the flash initiation button 113 of FIG. 1), and various visual, auditory, haptic, or other sensory feedback mechanisms that inform the user of operating or error conditions (e.g., whether the device 100 is suitable for treating a particular user's skin type, whether a maximum flash count has been exceeded, whether a replaceable light cartridge 116 (FIG. 1) or nosecap 118 are properly installed, whether an over-temperature condition has occurred, whether a power supply failure has occurred, and/or the like). In performing these functions, the user interface 108 interacts, directly or indirectly, with a control circuit 424 of the switching power supply 414 as more particularly described below.

The optical system 404 preferably includes one or more flash lamps 112, a reflector, a filter, and an optical waveguide 105, all contained within a handheld housing. As previously mentioned, the flash lamp(s) 112 and reflector (preferably mounted within about 1 millimeter of the flash lamps 112) are further contained within a replaceable light cartridge 116 that is inserted into the hand piece 104, while the filter and optical waveguide 105 are contained within the housing of the nose-cap 118 of the hand piece 104. In some embodiments, one or more reflective coatings can be applied directly to the exterior of the flash lamp(s) 112 to provide the desired wavelength filtration and/or to prevent undesirable light leakage at the electrode ends of the flash lamp(s) 112. Although these directly-applied coatings increase the cost and manufacturing complexity of the optical system 404, the overall optical emissions through the arc portion of the flash lamp(s) 112 are increased due to light recycling and light reclamation (i.e., the light which would otherwise have leaked out of the electrode ends of the flash lamp(s) 112 is reflected back into the desired optical path), thereby enabling a smaller quantity of electrical current to provide a given amount optical energy. In other embodiments, the reflective coatings are incorporated in a separate filter so that the additional heat generated as a result of any filtration does not further increase the thermal load of the flash lamp(s) 112—particularly beneficial when the flash lamps 112 are made of borosilicate rather than quartz or sapphire. Further, the optical waveguide 105 can be made of a solid, optically transparent material such as PMMA or can be configured as hollow, specular light pipe with interior reflective walls coated with silver (exhibiting, for example, a greater than 98% reflectance for wavelengths between about 600-1200 nanometers). When configured as a hollow light pipe, the optical waveguide 105 preferably includes parallel reflecting walls to minimize back reflections, as well as cut-out sections in two of its side walls so that the waveguide substantially encloses the arc portion of the flash lamp 112 (exemplary spacing between the waveguide 105 and envelope of the flash lamp(s) is preferably about 0.5 millimeters) while facilitating cooling of the electrode ends of the flash lamp 112.

The cooling system 406 includes at least one fan together with appropriately sized and positioned vents (e.g., as shown in FIGS. 1-3) to provide sufficient cooling for the device 100 over its intended operating range. Although a fan can be provided within the housing of the base 102 in order to cool the switching power supply 414, it is preferable to design the device 100 so that the switching power supply 414 is cooled passively and that the fan be primarily dedicated to cooling the flash lamps 112 and other elements in the hand piece 104.

In such preferred configurations, the fan can be configured to either blow air onto the flash lamps 112 or suck air over the flash lamps 112. The fan can also be a single speed fan that operates at full speed upon power-up of the device 100 or a variable speed fan that increases its air flow based on temperature measurements within the hand piece 104. The variable speed fan is preferred in situations where a relatively small region of skin is to be treated (e.g., up to about 60 square centimeters of a skin surface) since it results in relatively quiet operation of the device 100 that is more readily tolerated by its user. As the size of the treatment region increases, and the temperature within the hand piece 104 increases, the fan can be driven at a higher speed to maintain the safe operation of the device 100. For example, the fan can be operated at a relatively high speed when the temperature in the hand piece 104 exceeds about 40 degrees Celsius and at a slower speed when the temperature drops below about 35 degrees Celsius.

Further, the optical system 404 can be configured to facilitate cooling of the hand piece 104 without losing an excessive amount of energy due to light leakage. For example, a first end of the optical waveguide 105 can be positioned about 1 millimeter from the reflector and a second end can be positioned about 1 millimeter from an output window, thereby enabling some air flow to cool a surface of the window, as well as cool the interior of the hollow waveguide 105 and the reflector and arc portion of the flash lamp(s) 112, albeit with some loss in light energy. In one embodiment, the distance between one or more such elements can be made variable based on whether the flash lamp(s) 112 is being driven in a pulse state at that moment. For example, the distance between the optical waveguide 105 and the reflector and/or window can be decreased (e.g., to about 0.5 millimeters) or completely eliminated when the flash lamp(s) 112 is driven into a pulse state and otherwise remain at their original 1 millimeter positions, thereby minimizing light leakage during intense light emissions (e.g., during emission of a single light pulse or during emission of a light pulse sequence) and facilitating cooling during simmer or other operating states.

The temperature measurement system 408 includes one or more temperature sensors that can be positioned in the base 102 to measure the operating temperature of the switching power supply 414 and/or in the hand piece 104 to measure the operating temperature of the optical system 404. When positioned within the hand piece 104, the temperature sensor(s) is preferably located in the path of the exhaust air emitted by the cooling system 406 and that is further shielded from any substantial light emissions from the optical system 404. Upon detecting an over-temperature condition (e.g., at or above 50 degrees Celsius), the temperature measurement system 408 can generate a signal that causes the device 100 to either enter a cool down mode in which the switching power supply 414 is inhibited from driving the flash lamp(s) 112 into a pulse state, increase a time interval between successive light pulse sequences, and/or otherwise suspend normal operation until the measured temperature falls within a safe temperature range, which would likely be several degrees Celsius below the over-temperature threshold (e.g., 45 degrees Celsius).

The safety interlock system 410 detects whether the device 100 is properly positioned when treating a skin treatment region and whether it is properly assembled to prevent inadvertent exposure to hazardous electrical energy within the hand piece 104. For example, the safety interlock system 410 can include capacitive, optical, mechanical, bioimpedance, and/or other types of sensors in the vicinity of that portion of the nosecap 118 of the device 100 that is intended for placement substantially on or adjacent to the skin surface of a skin region to be treated. When a gliding motion is desired during a treatment session, it is preferable to couple a plurality of mechanical sensors to a frame forming part of the nosecap 118 that substantially surrounds the optical aperture of the device 100 (e.g., frame that holds the output window in desired position(s) within the optical path), which facilitates the gliding movement of the nosecap 118 when transitioning between adjacent skin treatment regions during a dermatologic treatment, rather than using individual sensors/plungers that are more amenable to stamping-type treatment movement and that are not as accommodating to gliding treatment motions. In an embodiment where the mechanical sensor is incorporated at least partly into the frame holding the window, the distance that such mechanical sensor is depressed preferably corresponds to the amount of decreased distance between the window and optical waveguide 105 as discussed above in connection with improving the optical efficiency of the device 100 during the pulse state of the flash lamp(s) 112. The safety interlock system 410 can also include a resistor (or other identification means) within the nosecap 118 that provides the basis for uniquely identifying authorized nosecaps and ensuring that any such nosecaps 118 are properly inserted into the handle 114 of the hand piece 104 before the switching power supply 414 applies any electrical energy to the optical system 404, thereby ensuring proper operation of the device 100 and reducing the risk of shock and optical hazards to a user.

The flash lamp characterization system 412 is preferably incorporated, at least partly, into the replaceable light cartridge 116 and includes a memory 413 that stores one or more characteristics of the flash lamp(s) 112 to ensure that the device 100 emits the desired amount of optical radiation during a dermatologic treatment session. The memory 413 is preferably a EEPROM element that provides non-volatile random memory access to stored flash lamp characteristics, such as a maximum number of flashes available for the flash lamp(s) 112, a current flash count for such flash lamp(s) 112, a range of wavelengths emitted by the flash lamp(s) 112 (particularly useful when the flash lamp(s) 112 include filter coatings on their exterior), an initial amount of electrical energy desired for driving the flash lamp(s) 112 into a pulse state, a first electrical compensation factor to adjust for reduced light output from the flash lamp(s) 112 as a result of aging, a second electrical compensation factor to adjust for the electrical-to-optical conversion efficiencies of particular flash lamp(s) 112 or flash lamp types, flash lamp 112 and cartridge manufacturing information (e.g., date, part number, etc.), an authorization code for the replaceable light cartridge 116, and/or the like.

The switching power supply 414 includes an AC line voltage detector 416 that detects locations within AC half cycles drawn from an AC line source 426 that are sufficient to provide the requisite electrical energy to drive the flash lamp(s) 112 to emit desirable levels of therapeutic light energy, a trigger power circuit 420 that instantiates ionization of the gas within the flash lamp(s) 112, a pulse-drive circuit 422 that provides the requisite electrical energy to drive the flash lamp(s) 112 to emit one or more desirable light pulse sequences that facilitate achievement of a desired dermatologic cosmetic effect in a skin treatment region, a simmer power circuit 418 that maintains the ionization of the gas within the flash lamp(s) 112 with a low current density between light pulses, and a control circuit 424 that controls and/or otherwise interacts with circuits, systems, and elements of the device 100 during operation of the device 100.

The AC line voltage detector 416 compares voltage levels of the electrical energy provided by the AC line source 426 against one or more reference voltages (reference voltages can be at a predetermined level or dynamically generated by the control circuit 424) that is indicative of a minimum operating voltage threshold. The AC line voltage detector 416 generates a signal that is transmitted to the control circuit 424 and is indicative of when the AC half cycle meets or exceeds the minimum operating voltage threshold. For example, the duty cycle of this signal can indicate when the minimum operating voltage threshold is met or exceeded by being "high" during the period of the AC half cycle that is at/above this threshold. Alternatively, the signal can be "low" during the period of the AC half cycle that is at/above the threshold and "high" only during transition periods between adjacent AC half cycles where the line voltage is below the threshold. Accordingly, the duty cycle or inverse of the duty cycle of the signal generated by the AC line voltage detector 416 is dynamically generated based on the then existing conditions of the AC line source 426 and provides timely information to the control circuit 424, which is subsequently used to time flash lamp emissions during that portion of the AC half cycle in which sufficient electric current can be drawn from the AC line source 426 to properly operate the flash lamp(s) 112 as desired. The device 100 can be configured to perform such voltage comparisons upon initial power-up and/or upon periodic intervals so as to dynamically determine changes in the AC line source 426 that may be caused by sagging, spiking, or other power-related fluctuations that may affect operation of the device 100 and for which such operation can be dynamically adapted to compensate for such fluctuations. An illustrative circuit for a suitable AC line voltage detector 416 is provided in FIG. 16 and is further discussed below.

Figure 14:
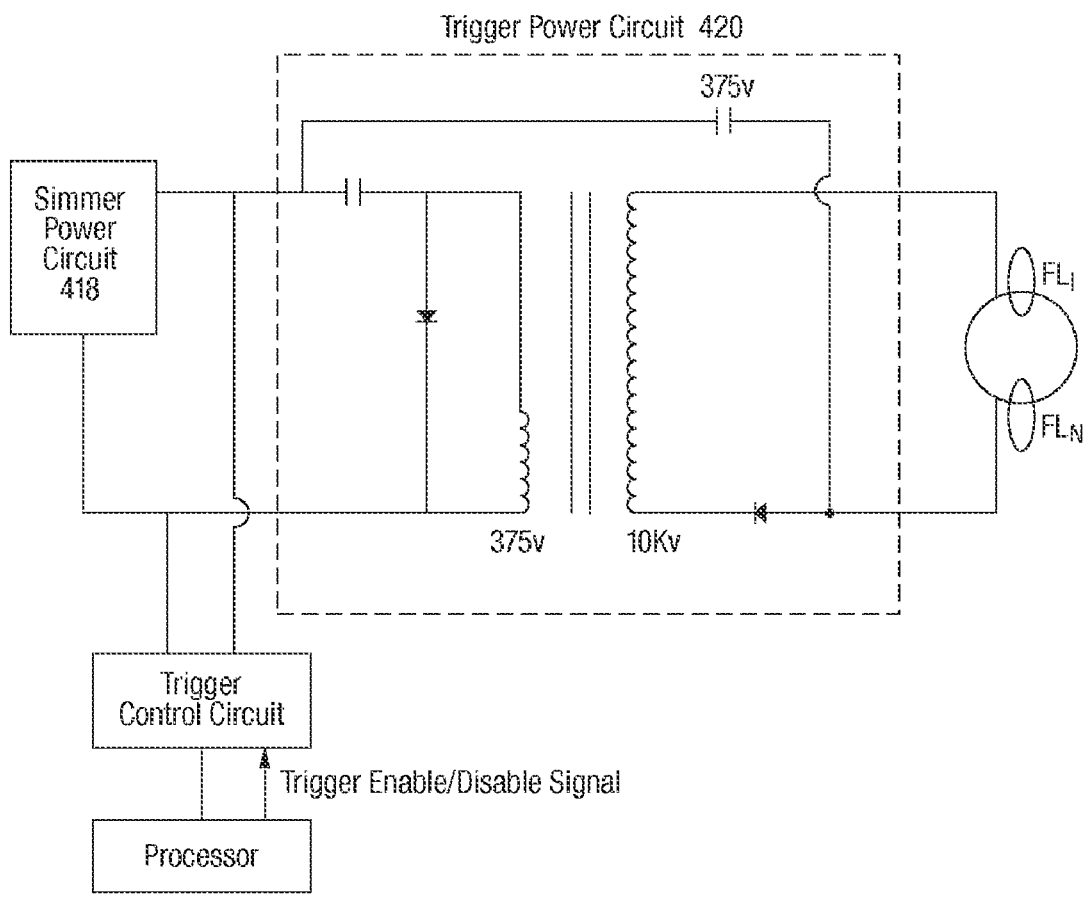
FIG. 14 provides a schematic of an illustrative trigger circuit of a power supply designed for operating a light-based dermatologic treatment device in accordance with an embodiment of the disclosed technology.

The trigger power circuit 420 is under the control of the control circuit 424 and includes a transformer that increases the input voltage of the electrical energy to about 6-10 kilovolts, which is of sufficient magnitude to trigger/instantiate ionization of the gas within the flash lamp(s) 112. For example, the control circuit 424 can enable the trigger power circuit 420 to instantiate ionization by applying a 10 kilovolt pulse of between about 200 nanoseconds-1 millisecond in duration to electrically-conductive, optically transparent coatings on at least part of an exterior of the flash lamp(s) 112 to capacitively couple this high voltage pulse into the flash lamp(s) 112 resulting in the ionization of the gas. In some embodiments, the input energy provided to the trigger power circuit 420 is drawn substantially directly from the AC line source 426. In another embodiment, the trigger power circuit 420 shares components with the simmer power circuit 418 so that the input electrical energy is drawn substantially from the simmer power circuit 418 and applied to trigger-dedicated components to generate the high voltage pulse. An illustrative trigger power circuit 420 made in accordance with such an embodiment is depicted in FIG. 14 and is more fully discussed below.

The pulse-drive circuit 422 is operated under the control of the control circuit 424 and includes a buck regulator that applies regulated, high density electrical current of, for example, between about 30-80 amps (more preferably between about 40-65 amps) to the electrodes of the flash lamp(s) 112 while the gas therein is ionized, resulting in intense light emissions that are suitable to facilitate achievement of a desired cosmetic effect in a skin treatment region. The regulated electrical current supplied to the flash lamp(s) 112 exhibits substantially the same profile as that desired for the light pulse sequences and is timed to coincide with that portion of the AC half cycle that is above a minimum operating voltage threshold as determined by the AC line voltage detector 416. In this manner, sufficient peak electrical current can be drawn from the AC line source 426 to support performance of the desired dermatologic treatment without unduly stressing external power circuits or requiring expensive capacitive circuit components.

Figure 13:
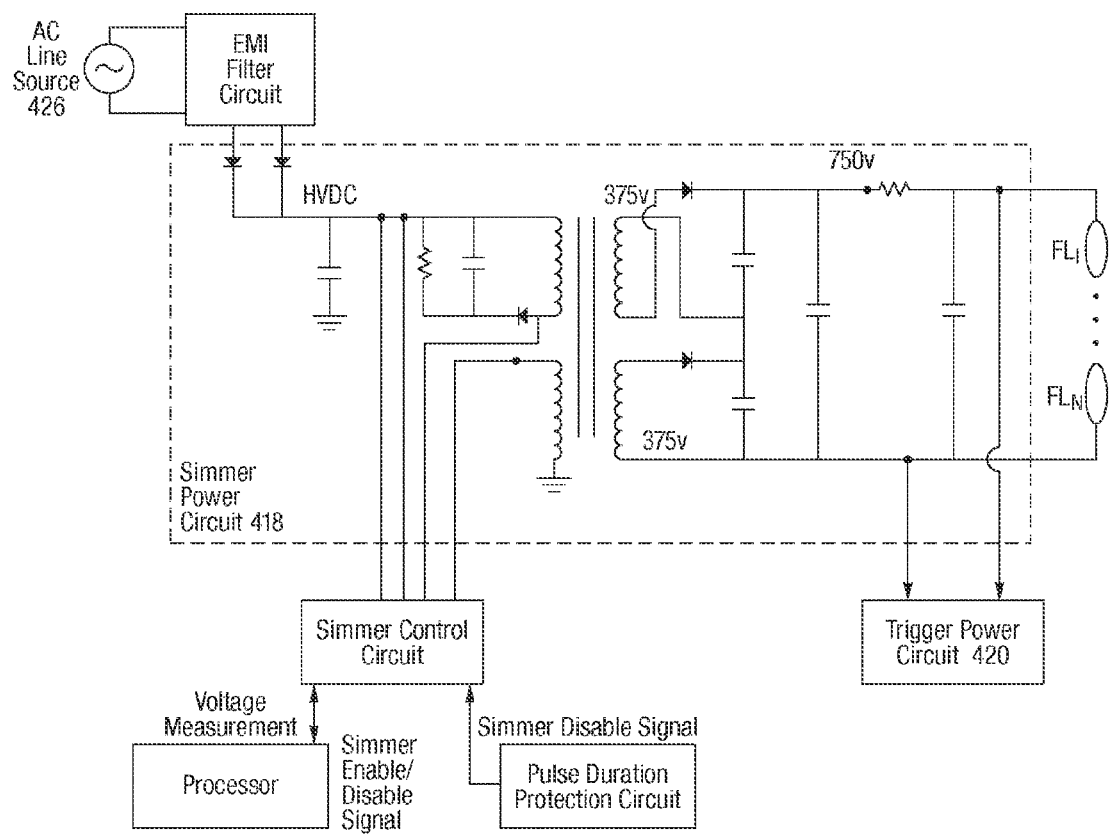
FIG. 13 provides a schematic of an illustrative simmer circuit of a power supply designed for operating a light-based dermatologic treatment device in accordance with an embodiment of the disclosed technology.

The simmer power circuit 418 is also operated under the control of the control circuit 424 and includes transformer and capacitor elements that apply a low current density (e.g., 50-100 milliamps) to the flash lamp(s) 112 between intense light pulse emissions. The transformer of the simmer power circuit 418 increases the input voltage from the AC line source 426 to about 750 volts for a dual flash lamp device (about 375 volts for a single flash lamp device) and applies this "simmer" energy to the flash lamp(s) before, during, and/or after the flash lamp pulse state. For example, in embodiments where components of the simmer power circuit 418 and trigger power circuit 420 are shared, the simmer energy is applied to the flash lamp(s) 112 in advance of the high voltage pulse provided by the trigger circuit, since the combination of the simmer and trigger voltages is sufficient to ionize the gas in the flash lamp(s) 112. Following ionization, the simmer energy can be applied at various times during operation of the device, such as continuously during individual light pulse sequences, during and between multiple light pulse sequences, during the inter-pulse delay intervals between individual pulses in a light pulse sequence, and/or the like. Those skilled in the art will recognize that a simmer power circuit 418 is not a requirement for proper operation of the dermatologic treatment device 100, but rather provides a mechanism to reduce the thermal and mechanical shock loads on the flash lamp(s). An illustrative simmer power circuit 418 is depicted in FIG. 13 and is more fully discussed below.

An illustrative control circuit 424 includes a processor to monitor and control operation of the device 100, along with current regulation circuitry to support operation of the pulse-drive circuit 422, simmer control circuitry to support operation of the simmer power circuit 418, trigger control circuitry to support operation of the trigger power circuit 420, and pulse duration protection circuitry to provide a safety mechanism that disables the device 100 in the event a component failure within the switching power supply 414 inadvertently results in excessive electrical energy being provided to the flash lamp(s) 112 that could result in undesirable light emissions therefrom. In brief overview, the control circuit 424 determines whether the device 100 is properly configured and capable of operating as designed when connected to a particular AC line source 426, and further operates the device 100 according to one or more user preferences to provide a therapeutically effective amount of optical radiation to one or more skin treatment regions during a dermatologic treatment session. The processor of the control circuit 424 executes algorithms and operates on data, variables, and other run-time components that are at least partially stored within such processor's memory and can best be described with reference to the illustrative methodology depicted in FIG. 5. Supporting hardware elements of an illustrative control circuit 424 are best understood with reference to FIG. 16 and its accompanying description below.

Figure 5:
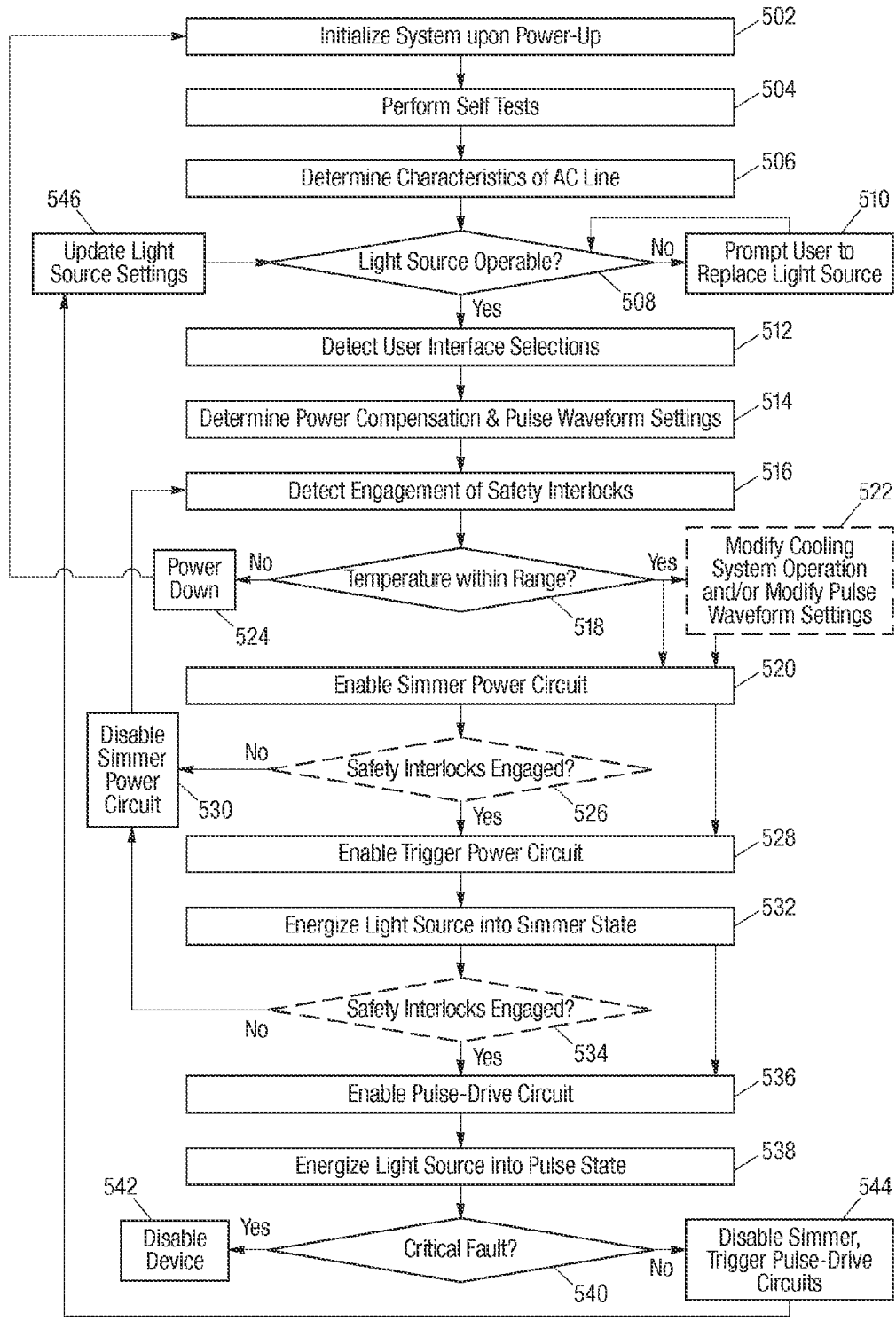
FIG. 5 provides a flow chart of an illustrative methodology for operating the dermatologic treatment device of FIG. 4 in accordance with an embodiment of the disclosed technology.

In one illustrative operation, and with reference now also to FIG. 5, an exemplary dermatologic treatment device 100, made and operated in accordance with at least some aspects of the disclosed technology, includes a control circuit 424 with a processor (e.g., PIC16F883 microcontroller, a product of Microchip Technology, Inc.) that executes stored instructions in a preemptive multitasking manner where non time-critical tasks are run in a state machine in the background and time critical tasks are run under interrupt priority in the foreground. Upon powering up, the processor initializes its internal clock, configures and initializes its input/output ports, initializes system drivers, initializes state values, enables interrupts, sets the state of light emitting diodes and other elements in the user interface 108, and otherwise initializes the device 100 (502).

The processor then performs self tests on the device 100 to ascertain whether it is in proper working condition (504). For example, the processor can evaluate signals or other indicia from i) the cooling system 406 to ensure that its fan is operating at the proper speed, ii) the temperature measurement system 408 to ensure that the device 100 can safely operate at its current temperature, iii) pulse duration protection circuitry in the control circuit 424 that determines whether one or more conditions exist within the pulse-drive circuit 422 or other elements of the switching power supply 414 that might result in driving the optical system 404 with excessive electrical energy that could be hazardous to a user and/or confirming that safety circuitry designed to prevent such hazardous conditions in the event of a hardware failure is operating properly, iv) the flash lamp characterization system 412 to ensure that the replaceable light cartridge 116 and flash lamp(s) 112 are authorized by the manufacturer of the device 100 and should therefore operate as intended and are properly installed within the device 100, v) the nosecap 118 to ensure that it is also authorized by the manufacturer and contains proper elements of the optical system 404 for a particular dermatologic treatment and is also properly installed within the device 100, and/or vi) the safety interlock system 410 to ensure that the device 100 is properly assembled/configured and that safety elements are in proper working condition such that a user is not exposed to hazardous electrical or optical conditions (which may occur, for example, when failed skin contact sensors are stuck in an engaged position thereby erroneously signifying that it is safe to emit intense light pulse emissions from the optical system 404).

The processor of the control circuit 424 determines the characteristics (e.g., frequency, high or low line conditions, sagging conditions, etc.) of the AC energy provided by the AC line source 426 by, for example, receiving one or more signals from the AC line voltage detector 416 representative of such characteristics (506). In one illustrative embodiment, the signal generated by such detector 416 includes at least two pulses, where the rising edge of the first pulse is substantially aligned with that portion of a first AC half cycle that is at the minimum operating voltage threshold following the peak of the half cycle and the falling edge of the first pulse is substantially aligned with that portion of the next adjacent, rectified AC half cycle (i.e., the second AC half cycle) that is at the minimum operating voltage threshold prior to the peak of that half cycle. Similarly, the rising edge of a second pulse is aligned with the minimum operating voltage threshold position on the decreasing slope of the second half cycle and the falling edge of the second pulse is aligned with the minimum operating voltage threshold position on the increasing slope of the third AC half cycle, and so forth. The time difference between the rising edges of the first and second pulses is indicative of the frequency of the AC energy provided by the AC line source 426, whereas the pulse width of each pulse (i.e., the time difference between the rising and falling edges of a given pulse) is indicative of high-line, low-line, or sagging power conditions. For example, a low-line condition on a 50 Hz AC line, would result in a 10 millisecond time difference between rising edges in adjacent pulses (8.3 millisecond time difference for a 60 Hz AC line) and with each pulse duration being somewhat longer than normal or high-line conditions. In ascertaining, the characteristics of the AC line, the processor of the control circuit 424 preferably averages the above time differences and pulse durations for multiple adjacent pulses (e.g., 32 adjacent pulses) to ensure that any outlier or erroneous measurements do not unduly affect the power and operational settings of the device 100.

The processor also accesses maximum flash count and current flash count information stored within a memory 413 of the flash lamp characterization system 412 to determine whether the flash lamp(s) 112 is/are still operable (i.e., have not yet exceeded the maximum flash count) (508). If the flash lamp(s) 112 is/are not operable, the processor causes the user interface 108 to prompt a user of the device 100 to replace such flash lamps (510). For example, the user interface can flash one or more light emitting diodes, beep, and/or otherwise indicate to the user that a replaceable light cartridge 116 containing such flash lamp(s) 112 needs to be replaced. The user interface 108 can also make the user aware of when the current flash count is approaching the maximum flash count so that the user can purchase another replaceable light cartridge in advance of end-of-life on the installed cartridge. If the flash lamp(s) 112 is/are operable, the processor evaluates signals or other indicia of the user interface 108 to detect selections made by or on behalf of a user of the device 100, such as dermatologic treatment type, power level settings, strobe versus pulse operating modes, skin/hair type settings, and/or the like (512).

The processor determines the power compensation and pulse waveform settings that are desirable for a particular dermatologic treatment based at least partly on the user selections, characteristics of the AC energy provided by the AC line source 426, and flash lamp characteristics (514). More particularly, the processor uses information pertaining to the dermatologic treatment type, power level settings, and/or skin/hair type settings to determine (based on computation and/or data structure lookup) the fluence, pulse durations, and/or inter-pulse/inter-sequence delays of one or more light pulses and/or light pulse sequences that are desirable for facilitating achievement of the desired dermatologic treatment. The processor further uses the AC line and flash lamp characteristics to determine the corresponding parameters of the electrical energy that is to be supplied by the switching power supply 414 to the optical system 404 to achieve the desired light profile. For example, sagging or low-line AC input conditions that exhibit periods of time in which voltage levels are low relative to nominal voltages require the application of higher electric currents to compensate for such low voltages and maintain a substantially constant power in the flash lamp(s) 112 and may also result in shorter pulse durations (in variable pulse embodiments) for each electrical pulse in the sequence of electrical pulses (which correspond to the light pulses in the light pulse sequence). Similarly, high-line AC input conditions provide higher voltages requiring lower currents to compensate for such high voltages in order to maintain a substantially constant power in the flash lamps(s) 112. Further, the aging and electric-to-light conversion characteristics of the flash lamp(s) 112 may necessitate additional modifications to the electric current provided to such flash lamp(s) 112. For example, the flash lamp aging/degradation characteristics for the flash lamp(s), which are stored in the memory 413 of the flash lamp characterization system 412 preferably include a predetermined percentage of light loss per some number of light pulses or light pulse sequences (e.g., a 5% loss in optical fluence for every 1000 light pulse sequences) that can be used to compute an electrical compensation value that increases the electric current to the flash lamp(s) 112 by an amount sufficient to compensate for this degradation, thereby achieving the desired, and substantially stable, optical fluence during the same or subsequent dermatologic treatment session. Similarly, the particular flash lamp(s) 112 installed within a replaceable light cartridge 116 may vary from cartridge to cartridge such that there may be a difference in the electric-to-optical conversion efficiency in such flash lamps 112, in which case a compensation factor stored within the memory 413 of the flash lamp characterization system 412 provides a mechanism by which the processor can adjust the electrical output of the switching power supply 414 to accommodate the desired light pulse sequence during the dermatologic treatment.

When a user of the device 100 presses the flash initiation button 113 of the user interface 108, the processor of the control circuit 424 detects such selection and, preferably while the button 113 is still being pressed, monitors the safety interlock system 410 to detect a signal therefrom indicative of when the skin contact sensors of the safety interlock system 410 are engaged, signifying that at least the portion of the hand piece 104 from which optical radiation is to be emitted is substantially in contact with or substantially surrounds the skin region to be treated (516). The processor then preferably accesses the temperature measurement system 408 and determines whether the temperature within the hand piece 104 and/or other locations within the device 100 are within a manageable temperature operating range (518). If the temperature is below a first temperature threshold signifying a safe operating temperature, the processor can instruct simmer control circuitry within the control circuit 424 to enable the simmer power circuit 418 (520). If the temperature is within the manageable temperature operating range, between the first temperature threshold and a second temperature threshold, the processor can optionally decide whether to modify operation of the cooling system 406 (e.g., increase the speed of a variable speed fan within the hand piece 104 or elsewhere in the device 100) and/or modify parameters associated with the light pulse sequences and/or associated electrical pulses (e.g., increase the time interval between successive light pulse sequences thereby at least temporarily decreasing the overall flash rate of the device 100) so that the temperature within the device stays within desired temperature limits during and/or immediately following the next light pulse sequence (522). If the measured temperature exceeds the higher of the two temperature thresholds, signifying an unsafe operating condition, the processor can issue a signal to the switching power supply 414 that powers down the device 100 (524).

In one embodiment, it takes about 125 milliseconds after the simmer power circuit 418 is enabled for the circuit 418 to reach its full output voltage (of about 750 volts for a dual flash lamp device), in which case the processor uses its internal clock to measure this time period and suspends any further power-related activities until this time period lapses. Once the simmer power circuit 418 achieves its desired output voltage, the processor can optionally check whether the safety interlocks remain engaged (526) or proceed with sending a signal to trigger control circuitry of the control circuit 424 to enable the trigger power circuit 420 (528). If the processor detects that the safety interlocks are no longer engaged, it can issue a signal to the simmer control circuitry that disables the simmer power circuit 418 (530).

As previously mentioned, it is preferable that the simmer power circuit 418 and trigger power circuit 420 share components such that the simmer output voltage is added/transformed to the trigger power voltage (e.g., between about 6-10 kilovolts) to reach a sufficient magnitude in aggregate to trigger/instantiate ionization of the gas within the flash lamp(s) 112, which marks the beginning of the flash lamp's simmer state (532). Following ionization, the simmer state can be maintained by continuing to apply between about 50-100 milliamps of electric current to the flash lamp(s) from the simmer power circuit 418. The processor can then optionally check whether the safety interlocks remain engaged (534) or proceed by sending a signal to current regulator circuitry of the control circuit 424 to enable the pulse-drive circuit 422 (536). If the safety interlocks were no longer engaged, the processor can issue a signal to the simmer control circuitry that disables the simmer power circuit 418, which would effectively terminate the simmer state of the flash lamp(s) 112.

The processor issues signals and provides reference voltages to the current regulator circuitry that drive the pulse-drive circuit 422 of the switching power supply 414 to generate pulses of electrical energy, which substantially mirror the shape and other attributes of the light pulse sequences, and that energize the flash lamp(s) 112 while in a simmer state to emit intense pulsed light emissions during the lamp's pulse state (538). As previously discussed, the electrical energy provided by the pulse-drive circuit 422 to energize the flash lamp(s) 112 from a simmer state into their pulse state is drawn substantially from the AC line source 426 during periods within the AC half cycle that are above a minimum operating voltage threshold. This portion of the AC half cycle is also capable of providing the desired peak current levels necessary to drive the flash lamp(s) during their pulse state without drawing any substantial energy from any charged capacitors. The shape (e.g., pulse duration, inter-pulse delay intervals, degree of electrical current oscillation about a nominal current value and within upper and lower limits) and size (e.g., peak and average electrical current) of the electrical pulses and sequences of electrical pulses generated by the pulse-drive circuit 422 can be maintained within a desired pulse profile determined by the processor. More particularly, the processor issues signals to the current regulator circuitry that selectively enable a field-effect transistor or other power switching element in the buck regulator circuitry of the switching power supply 414 to conduct electrical energy to the flash lamp(s) 112. Since many dermatologic treatments are preferably performed with substantially square light profiles, the processor can control the power switching element to selectively conduct or inhibit electrical energy transmissions, such that the electrical energy provided to the flash lamp(s) oscillates (e.g., at between a 50-100 kilohertz rate and more preferably at about an 80 kilohertz rate) about a desired current level and within upper and lower current limits so that the current is substantially regulated. The processor enables or disables the power switching element based at least partly on the amount of current that passes through the flash lamp(s) 112 at a given moment during the pulse state (determined via, for example, a current sensing resistor), which affects the magnitude of the current oscillation about the desired level (e.g., between about 35-80 amps, and more preferably between about 47-65 amps+/−10 amps), and on the duty cycle or inverse of the duty cycle of the signal generated by the AC line voltage detector during periods within the AC half cycles that are at or above the minimum operating voltage thresholds (used to transition between pulse and simmer states of the flash lamp(s) 112 during and after electrical/light pulse sequences).

The control circuit 424 of the switching power supply 414 can detect one or more critical faults that may occur as a result of a hardware or software malfunction during or after emission of a light pulse sequence (540). For example, a failure of the power switching element that shorts the element into a continuously conducting state could result in excessive, unregulated electrical energy driving the flash lamp(s), which could result in undesirable light emissions during the lamp's pulse state. If a critical fault (i.e., unrecoverable fault condition) occurs, the processor, pulse duration protection circuitry and/or other circuitry within the control circuit 424 can use an IGBT or other switching element to permanently or temporarily disable the device 100 (542). In one embodiment, the device 100 is permanently disabled after a critical fault condition repeats itself several times within a given time period. If a critical fault condition does not occur and the light pulse sequence is successfully emitted, then the processor can instruct the control circuit 424 to disable the simmer, trigger, and pulse-drive circuits 418-422 (544) and to update the current flash count or other flash lamp characteristics stored in the memory 413 of the flash lamp characterization system 412 (546) in preparation for subsequent operations of the device 100.

It is important to note that the illustrative methodology depicted in FIG. 5 and described above can be modified in various ways without materially departing from the benefits of the disclosed technology. By way of non-limiting example, the methodology described in blocks 502-518 can be combined in whole or in part or performed in different sequences; determinations of when safety interlocks are engaged need not occur in the time period beginning with the simmer state and ending upon termination of the pulse state of the flash lamp(s) 112; the simmer state can be completely avoided by operating the flash lamp(s) in their pulse state substantially immediately following emission of the trigger pulse; and/or the simmer state of the flash lamp(s) can continue beyond termination of the pulse state and thus during the period of time between adjacent light pulse sequences.

With reference now also to FIGS. 6-12, illustrative electrical, optical, and thermal waveforms are shown, which may be encountered in an illustrative dermatologic treatment session directed to temporary hair removal using an exemplary dermatologic treatment device 100 made and operated in accordance with at least some aspects of the disclosed technology. More particularly, FIG. 6 depicts a full wave rectified AC power signal (with a 50 Hz frequency and a corresponding 10 millisecond period) exhibiting either a high-line condition 602 or a low-line condition 604. The nominal AC voltage condition is not shown so as to avoid unduly cluttering the figure, but those skilled in the art recognize that such nominal voltage waveform would be located between the high and low-line waveforms 602, 604. An illustrative minimum operating voltage threshold 606 is also depicted and the intersection of such threshold 606 with the high-line waveforms 602 shows that the duration of that portion of the AC half cycle above the threshold 606 is greater than the corresponding duration of the low-line waveform 604. Accordingly, high-line AC conditions can accommodate longer electrical and light pulse widths and lower peak currents required for a particular dermatologic treatment than low-line AC conditions.

FIG. 7 depicts an illustrative signal 702 that may be formed by the AC line voltage detector 416 to assist the processor of the control circuit 424 in its determination of AC line frequency and durations within the AC half cycles that meet or exceed the minimum operating voltage threshold 606. In the illustrated embodiment, each pulse in the signal 702 is indicative of when the voltages of the AC half cycles are below the minimum operating voltage threshold 606. Note that the duration of such pulses are shorter for high-line AC conditions than for low-line AC conditions, in which case the inverse of the depicted duty cycle identifies that portion of the AC half cycle that can provide sufficient electrical energy to drive the flash lamp(s) 112 (from a simmer state into a pulse state) of the dermatologic treatment device 100 during a treatment session without drawing any substantial electrical energy from a charged capacitor. In another embodiment, the AC line voltage detector 416 can generate a signal that is the inverse of the depicted signal 702 in which case its duty cycle would substantially directly reflect that portion of the AC half cycles capable of driving the flash lamp(s) 112 in the disclosed manner.

FIG. 8 provides a signal diagram of an illustrative voltage waveform 802 that may be applied across dual flash lamps of a dermatologic treatment device during a temporary hair removal treatment session in which an AC high-line condition exists. In this embodiment, the simmer power circuit 418 initially applies about 750 volts to the flash lamps, which is subsequently combined with the voltage provided by the trigger power circuit 420 to achieve a 10 kilovolt trigger signal in aggregate that is sufficient to capacitively trigger/instantiate ionization of the gas in the flash lamps. The control circuit 424 then causes the pulse-drive circuit 422 to convey voltage pulses to the flash lamps substantially during the duration of the AC half cycle above the minimum operating voltage threshold 606 (in this case, for a duration of about 7 milliseconds), where such voltage pulses are separated by about 3 milliseconds during which a simmer voltage is maintained across the flash lamps. As shown the voltage pulses can exhibit a substantially square profile with an oscillation of about +/−25 volts about the average voltage of 100 volts.

FIG. 9 provides a signal diagram of an illustrative electric current waveform 902 corresponding to the voltage waveform 802 of FIG. 8. In this embodiment, a low level current of about 100 milliamps begins to flow across the flash lamp(s) upon instantiation of ionization of the gas in the flash lamp(s) and such low level current continues to flow in the inter-pulse period to ensure that the gas remains ionized at least until the corresponding light pulse sequence is completed. During the pulse state of the flash lamp(s), the current increases to about 50 amps and is maintained within about +/−10 amps of that level as a result of the 80 kilohertz switching action of the pulse-drive circuit 422 as previously described. In a related embodiment that further reduces thermal and mechanical shocks to the flash lamp(s), the aggregate pulse width of the current waveform 902 can be extended (e.g., to between about 50-250 ms, preferably between about 60-130 ms, and most preferably to about 110 ms in total) such that additional regulated current at a moderate intensity level (e.g., between about 1-25 amps, preferably between about 1-15 amps) is applied continuously to the flash lamp(s) during a period following ionization of the flash lamp(s) and up to the intense light emissions occurring at the 50 amp current level. This moderate current level not only stabilizes the temperature and reduces the mechanical stresses of the flash lamp(s), but also serves to preheat target tissue in a skin treatment region without causing any substantial damage to non-target, surrounding tissue.

FIG. 10 provides a signal diagram of an illustrative light pulse sequence 1002 corresponding to the current waveform 902 of FIG. 9. In this embodiment, the intense light emissions that occur during the pulse state of the flash lamps are substantially aligned with the pulse durations of the electrical current waveform 902 and exhibit corresponding oscillations in light output. In a temporary hair removal treatment session, each of the four depicted light pulses (exhibiting wavelengths of interest) can emit about 3.75 joules of optical radiation for an aggregate of 15 joules, which can be applied via a 2 square centimeter aperture to the skin resulting in a fluence of about 7.5 joules per square centimeter. Of course, the number of pulses, energy per pulse, inter-pulse period, and other aspects of this illustrative waveform 1002 and those of its related electrical waveforms 802, 902 can be readily modified without materially departing from the teachings of the disclosed technology, so long as the intense light emissions during the lamps' pulse states and corresponding electric current and voltage pulses occur substantially within the time period in which the AC half cycles are at or above the minimum operating voltage threshold 606.

FIG. 11 provides an illustrative thermal profile 1102 of target tissue (e.g., hair follicle, hair bulge, etc.) when subjected to the light pulse sequence 1002 of FIG. 10 during a temporary hair removal treatment session. As shown, the temperature of the target tissue increases substantially during each light pulse and remains substantially at the same temperature or slightly decreases during the inter-pulse period between such light pulses. The aggregate effect of such light pulses is to increase the temperature of the target tissue to a level at which temporary hair removal will result.

Similarly, FIG. 12 provides an illustrative thermal profile 1202 of non-target tissue, such as the epidermis, when subjected to the light pulse sequence 1002 of FIG. 10 during a temporary hair removal treatment session. As with the temperature profile 1102 of target tissue, the temperature of the epidermis is increased during each light pulse, but decreases more rapidly than the target tissue during the inter-pulse period. Accordingly, the temperature of the epidermis during the dermatologic treatment session can be maintained below any significant damage threshold, while the desired thermal protocol is applied to the target tissue.

FIG. 13 depicts the circuit components and interconnections of an illustrative simmer power circuit 418 that can be made and operated in accordance with the disclosed technology. As shown, and under the control of the processor, simmer control circuit, and/or pulse duration protection circuit of the control circuit 424, the simmer power circuit 418 includes a transformer that increases the voltage level of direct current formed from the alternating current of the AC line source 426 to a desired level (750 volts for a dual flash lamp device). The simmer power circuit 418 also includes a variety of capacitors that smooth out the simmer power that is subsequently applied to the flash lamps 112 before and during their simmer state.

FIG. 14 depicts the circuit components and interconnections of an illustrative trigger power circuit 420 that can be made and operated in accordance with the disclosed technology. As shown, and under the control of the processor and trigger control circuitry of the control circuit 424, the trigger power circuit 420 obtains some of the higher voltage energy from the transformer of the simmer power circuit 418 and further increases its voltage to about 10 kilovolts using its own transformer. The resulting trigger pulse can then be used to capacitively trigger the flash lamps 112 to instantiate their simmer state as previously described.

Figure 15:
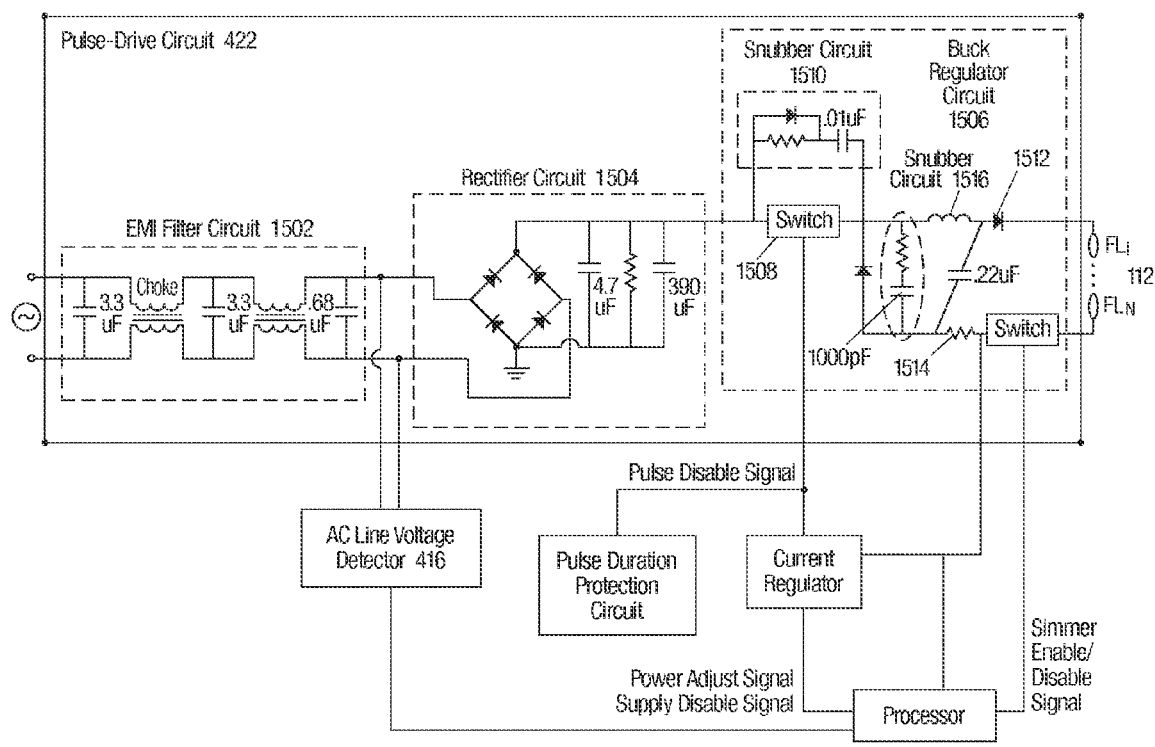
FIG. 15 provides a schematic of an illustrative pulse-drive circuit of a power supply designed for operating a light-based dermatologic treatment device in accordance with an embodiment of the disclosed technology.

FIG. 15 depicts the circuit components and interconnections of an illustrative pulse-drive circuit 422 that can be made and operated in accordance with the disclosed technology. The pulse-drive circuit 422 includes EMI filter circuitry 1502, rectifier circuitry 1504, and buck regulator circuitry 1506. The EMI filter circuit 1502 includes one or more chokes and capacitive elements that effectively filter the electrical energy to/from the AC line source 426 from electromagnetic interference. The filtered electrical energy can then be applied across a diode bridge of the rectifier circuit 1504 to full wave rectify the alternating current and then the rectified energy is applied to capacitive elements within the circuit 1504 to smooth out the rectified AC into a high voltage direct current waveform. This high voltage direct current can then be applied to a field effect transistor or other power switching element 1508, which is selectively driven into conductive and nonconductive states under the control of the processor, current regulation circuitry, and/or pulse duration protection circuitry of the control circuit 424 as previously described. A snubber circuit 1510 can be used across the power switching element 1508 to prevent ringing in the switch during operation of the device 100. When the switch 1508 is in a conducting state, the electrical energy is passed through an inductor and diode circuit and applied to the electrodes of the flash lamps 112. The diode 1512 inhibits any substantial electrical energy from entering the pulse-drive circuit 422 from the simmer power circuit 418 when the simmer circuit is engaged and thus prevents potential damage to circuit components of the pulse-drive circuit 422. A current sensing resistor 1514 in the conducting path provides indicia to the processor and/or current regulator of the electrical current that is flowing through the flash lamps 112 at any given time and thus serves as a basis for the control circuit 424 to selectively enable/disable the switch 1508, thereby controlling the electrical energy emissions to the flash lamps 112 that drive the light pulse sequence emissions.

Figure 16:
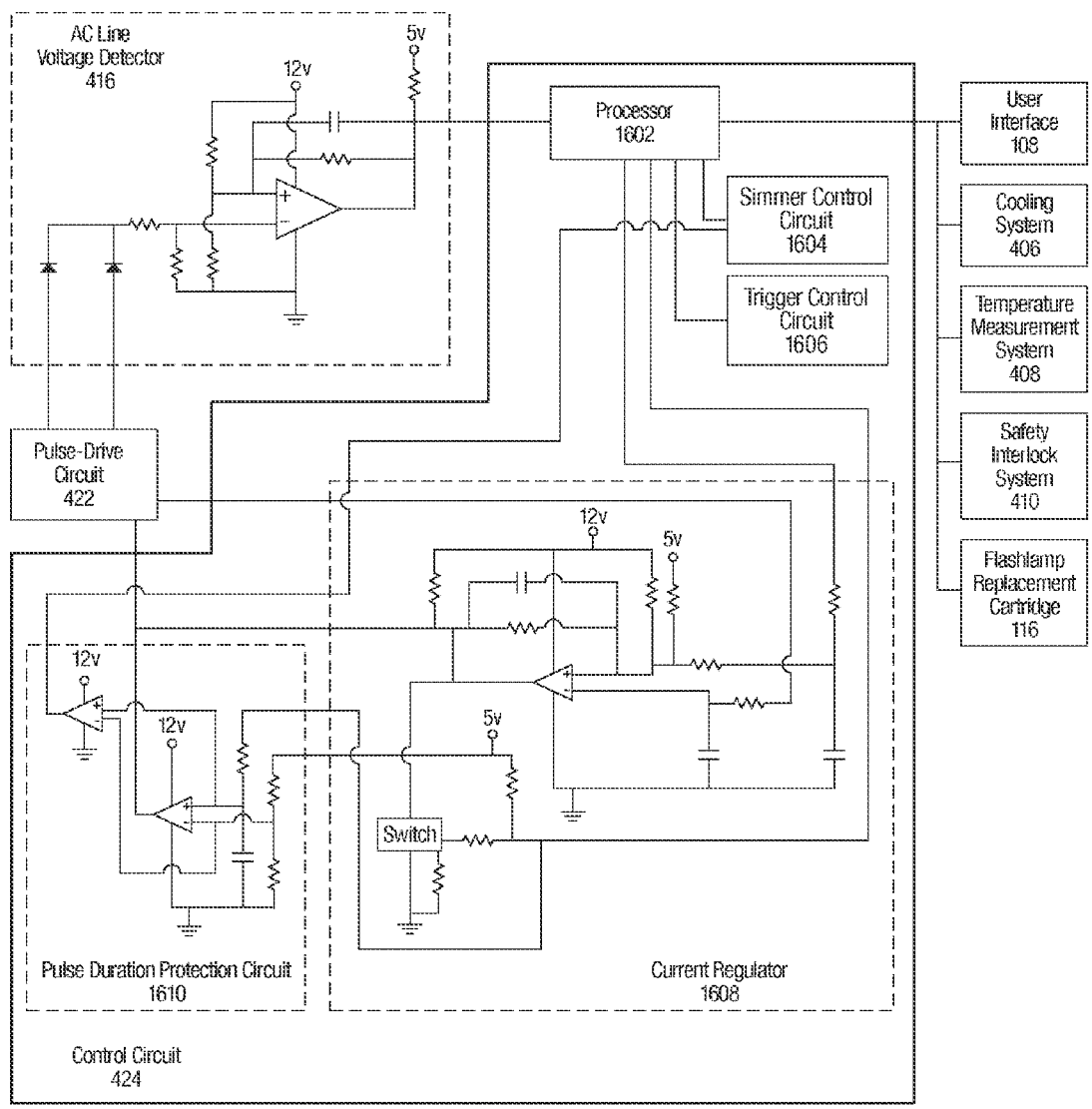
FIG. 16 provides a schematic of an illustrative control circuit of a power supply designed for operating a light-based dermatologic treatment device in accordance with an embodiment of the disclosed technology.

FIG. 16 depicts the circuit components, interconnections, and interfaces of an illustrative control circuit 424 and AC line voltage detector 416 that can be made and operated in accordance with the disclosed technology. The control circuit 424 includes a processor 1602, a simmer control circuit 1604, a trigger control circuit 1606, a current regulator 1608, and a pulse duration protection circuit 1610, all of which are designed and configured to operate the device 100 in accordance with the disclosed embodiments.

While a number of embodiments and variations thereon have been described above, it is intended that these embodiments are for purposes of illustration only and that numerous other variations are possible while practicing the teachings of the disclosed technology. For example, the disclosed technology has been largely described in connection with hair growth management/removal applications, but can be applied to a wide variety of medical or cosmetic dermatologic treatments. The particular circuit configurations and related functionality are also illustrative and can be readily modified without materially departing from the teachings of this disclosure. Thus, while the invention has been particularly shown and described above with reference to preferred embodiments, the foregoing and other changes in form and detail may be made therein by one skilled in the art without departing from the spirit and scope of the invention which is to be defined only by the appended claims.

What is claimed is:

1. A dermatologic treatment device, the device comprising:
   at least one pulse-able flash lamp capable of emitting sufficient light energy to facilitate achievement of a desired cosmetic effect in a skin region; and
   a reflector optically coupled to the flash lamp and adapted to reflect at least some of the light energy emitted by the flash lamp;
   an optical waveguide optically coupled to the reflector and adapted to convey at least some of the reflected light energy therefrom; and
   an optically transparent window optically coupled to the optical waveguide and adapted to receive at least some of the light energy conveyed thereby, wherein at least a portion of the optical waveguide is spaced apart from the window by a predetermined distance when the flash lamp is not in its pulse state and wherein the distance is substantially eliminated when the flash lamp is in its pulse state.

2. The dermatologic treatment device of claim 1, wherein the flash lamp emits at least one sequence of light pulses during its pulse state.

3. The dermatologic treatment device of claim 1, wherein the distance between the optical waveguide and at the window facilitates cooling of the device, and wherein the substantially eliminated distance temporarily decreases cooling of a least part of the device in favor of improving optical efficiency of the device.

\* \* \* \* \*